United States Patent
Shi et al.

(10) Patent No.: US 6,680,132 B2
(45) Date of Patent: Jan. 20, 2004

(54) RED ORGANIC ELECTROLUMINESCENT DEVICES

(75) Inventors: Jianmin Shi, Webster, NY (US); Kevin P. Klubek, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/105,683

(22) Filed: Mar. 25, 2002

(65) Prior Publication Data

US 2003/0203234 A1 Oct. 30, 2003

(51) Int. Cl.⁷ ................................ H05B 33/14
(52) U.S. Cl. ................ 428/690; 428/917; 313/504
(58) Field of Search .................. 428/690, 917; 313/504; 546/947; 549/426

(56) References Cited

U.S. PATENT DOCUMENTS

| 4,769,292 A | 9/1988 | Tang et al. ............. 428/690 |
| 5,908,581 A | 6/1999 | Chen et al. ........... 252/301.16 |
| 5,935,720 A | 8/1999 | Chen et al. ............. 428/690 |

FOREIGN PATENT DOCUMENTS

EP 1 235 467 A2 * 8/2002

* cited by examiner

Primary Examiner—Marie Yamnitzky
(74) Attorney, Agent, or Firm—Raymond L. Owens

(57) ABSTRACT

An organic EL device, having an anode and a cathode, and at least one organic luminescent medium including a compound of the formula:

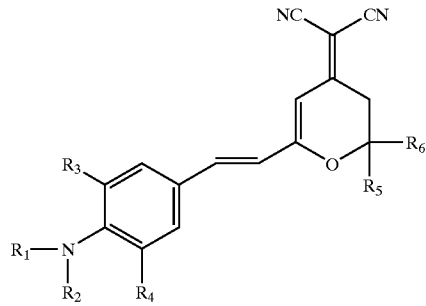

wherein:

R1 and R2 are individually alkyl of from 1 to 20 carbon atoms, aryl, substituted aryl, carbocyclic and other heterocyclic systems; and R1 and R2 can be connected to form 5 or 6 member ring systems; and R3 and R4 are individually hydrogen; alkyl of from 1 to 10 carbon atoms, and a branched or unbranched 5 or 6 member substituent ring connecting with R1, R2 respectively; and R5 and R6 are individually hydrogen; alkyl of from 1 to 20 carbon atoms; aryl and heteroaryl of from 5 to 24 carbon atoms; and R6 can be connected with R5 to form a branched or unbranched 5 or 6 member carbocyclic ring.

5 Claims, 3 Drawing Sheets

RED ORGANIC ELECTROLUMINESCENT DEVICES

FIELD OF INVENTION

This invention relates to organic electroluminescent (EL) devices. More specifically, this invention relates to stable and saturated red emission EL devices.

BACKGROUND OF THE INVENTION

Organic light emitting diodes (OLEDs), also known as organic electroluminescent devices, are a class of electronic devices which emit light in response to an electrical current applied to the device. Organic EL devices are also known to be highly efficient and are capable of producing a wide range of colors. Useful applications such as flat panel displays have been contemplated. While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322–334, 1969; and Dresner U.S. Pat. No. 3,710,167, issued Jan. 9, 1973. The organic layers in these devices, usually composed of a polycyclic aromatic hydrocarbon, were very thick (much greater than 1 µm). Consequently, operating voltages were very high, often >100 V.

More recent organic EL devices include an organic EL element consisting of extremely thin layers (e.g. <1.0 µm) between the anode and the cathode. Herein, the organic EL element encompasses the layers between the anode and cathode electrodes. Reducing the thickness lowered the resistance of the organic layer and has enabled devices that operate at much lower voltages. In a basic two-layer EL device structure, described first in commonly-assigned U.S. Pat. No. 4,356,429, one organic layer of the EL element adjacent to the anode is specifically chosen to transport holes, therefore, it is referred to as the hole transport layer, and the other organic layer is specifically chosen to transport electrons, referred to as the electron transport layer. The interface between the two layers provides an efficient site for the recombination of the injected hole/electron pair and the resultant electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610–3616, 1989]. The light-emitting layer commonly consists of a host material doped with a guest material. Still further, there has been proposed in commonly-assigned U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

For the production of full-color EL display panel, it is necessary to have efficient red, green and blue (RGB) EL materials with proper chromaticity and sufficient luminance efficiency. The guest host doped system offers a ready avenue for achieving such an objective, mainly because a single host with optimized transport and luminescent properties may be used together with various guest dopants leading to EL of desirable hue.

A doped EL system based on the principle of guest host energy transfer to effect the spectral shift from tris(8-hydroxyquinolinato)aluminum (Alq) to the dopant molecules has been disclosed by Tang et al [commonly-assigned U.S. Pat. No. 4,769,292]. Alq is a suitable host for red EL emitters since its emission at 530 nm is adequate to sensitize guest EL emission in the red spectral region. The preferred dopants chosen to provide the red emission in this prior art were 4-(dicyanomethylene)-2-methyl-6-(pdimethylaminostyryl)-4H-pyran (DCM) and the julolidyl derivatives DCJT and DCJTB.

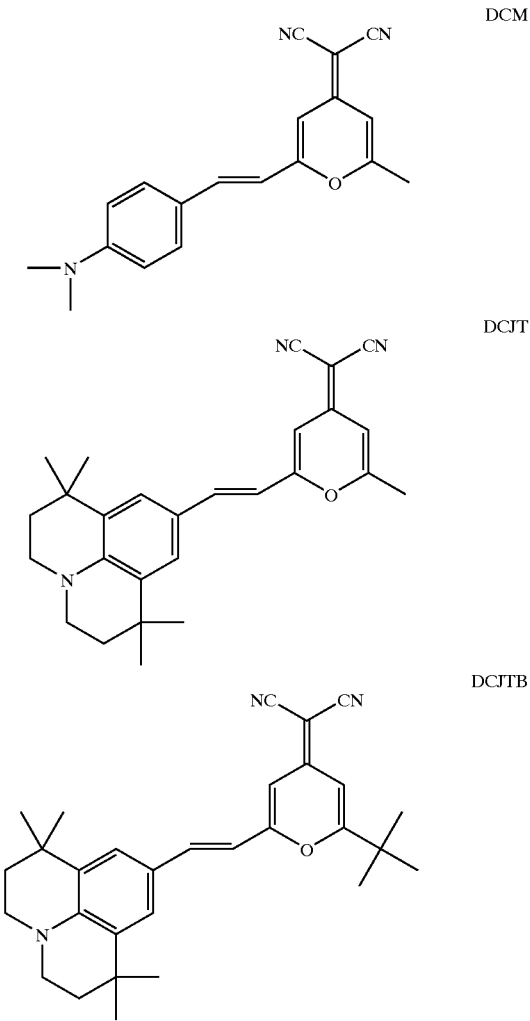

These molecules generally have a high photoluminescence (PL) quantum yield and the position of the emission maxima can be readily shifted by certain modification of the DCM structure. However, the luminance efficiency of the Alq/DCM system is compromised by two factors. First, the spectral bandwidth of the emission is rather broad. As a result, a suitable red hue can be obtained only with the dominant emission in the deep red region. The broadness of the emission band yields a significant portion of photons in the long wavelength spectral region where the eye is not sensitive resulting in a loss of luminance efficiency. Second, the EL efficiency of the guest host system is highly dependent on the concentration of the guest in the host matrix. The concentration quenching effect, presumably due to the aggregation of guest molecules, is relatively strong in the Alq/DCM system. A further loss in luminance efficiency would result if a concentrated guest host system is necessary to provide for an adequate red hue in the EL emission.

SUMMARY OF THE INVENTION

It is an object of the present invention to provide an improved red emitting organic EL device.

It is an another object of the present invention to provide a red emitting device for full color organic EL device.

These objects are achieved by an organic EL device, comprising an anode and a cathode, and at least one organic luminescent medium including a compound of the formula:

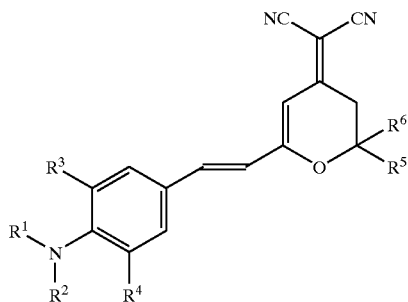

wherein:
R1, and R2 are individually alkyl of from 1 to 20 carbon atoms, aryl, substituted aryl, carbocyclic and other heterocyclic systems; and R1, and R2 can be connected to form 5 or 6 member ring systems; and R3, and R4 are individually hydrogen; alkyl of from 1 to 10 carbon atoms, and a branched or unbranched 5 or 6 member substituent ring connecting with R1, R2 respectively; and R5 and R6 are individually hydrogen; alkyl of from 1 to 20 carbon atoms; aryl and heteroaryl of from 5 to 24 carbon atoms; and R6 can be connected with R5 to form a branched or unbranched 5 or 6 member carbocyclic ring.

It is a feature of the present invention that EL devices made using compounds in accordance with the above structure produce an improved and highly saturated red hue.

BRIEF DESCRIPTION OF THE DRAWINGS

These and other advantages of this invention can be better appreciated by reference to the following detailed description considered in conjunction with the drawings in which.

DETAILED DESCRIPTION OF THE INVENTION

Figure 1:
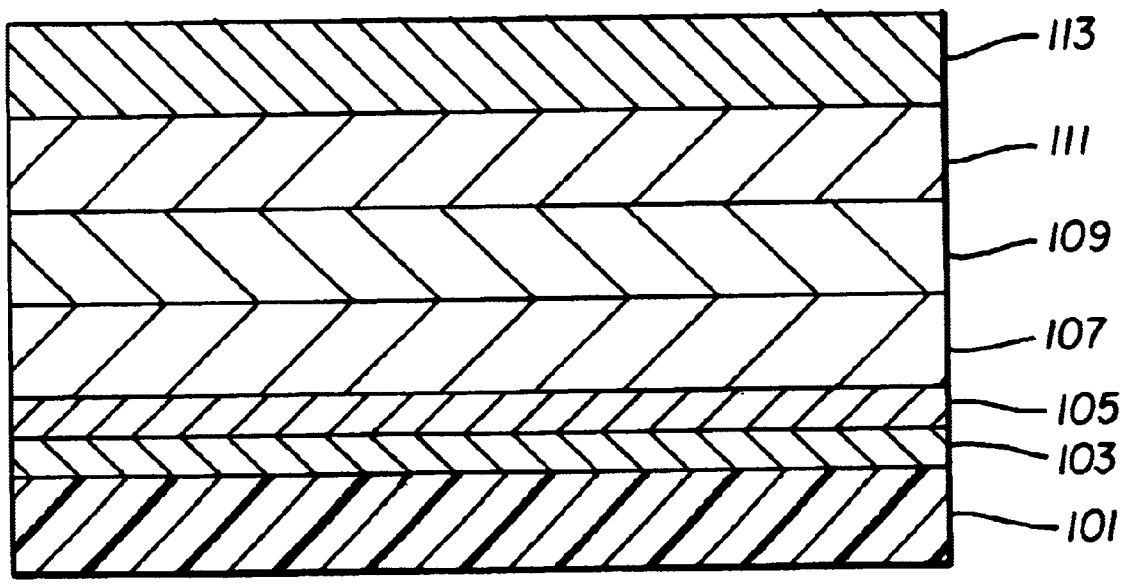
FIG. 1 is a schematic diagram of the multilayer structures of preferred EL devices which can employ the compound of this invention.
Figure 2:
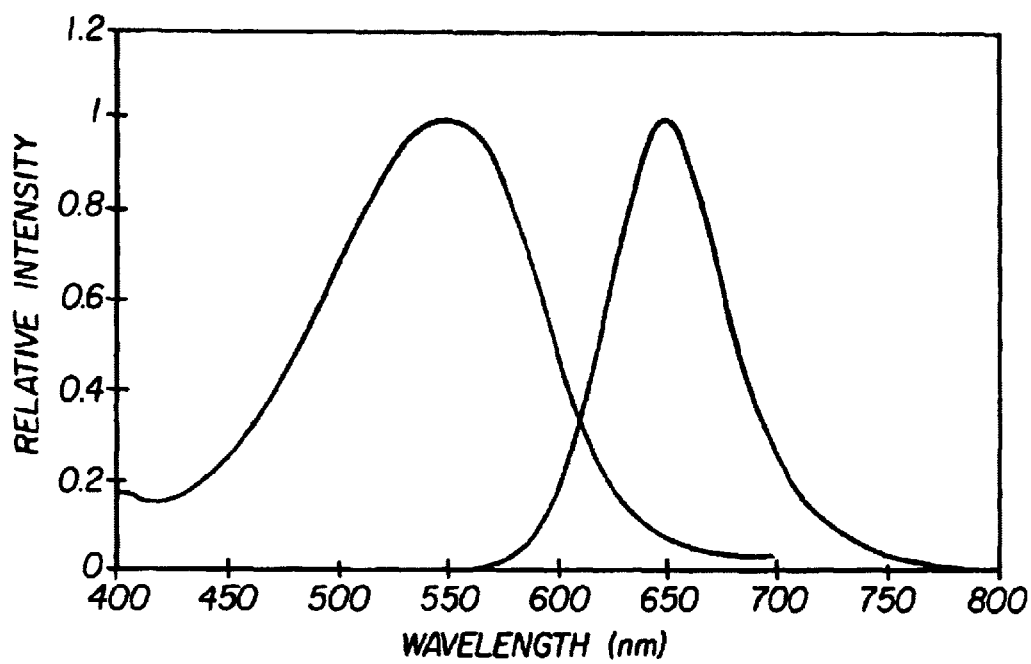
FIG. 2 shows the plot of the absorption and emission spectral characteristics of the compound TJDCP (III-08) in accordance with the present invention.
Figure 3:
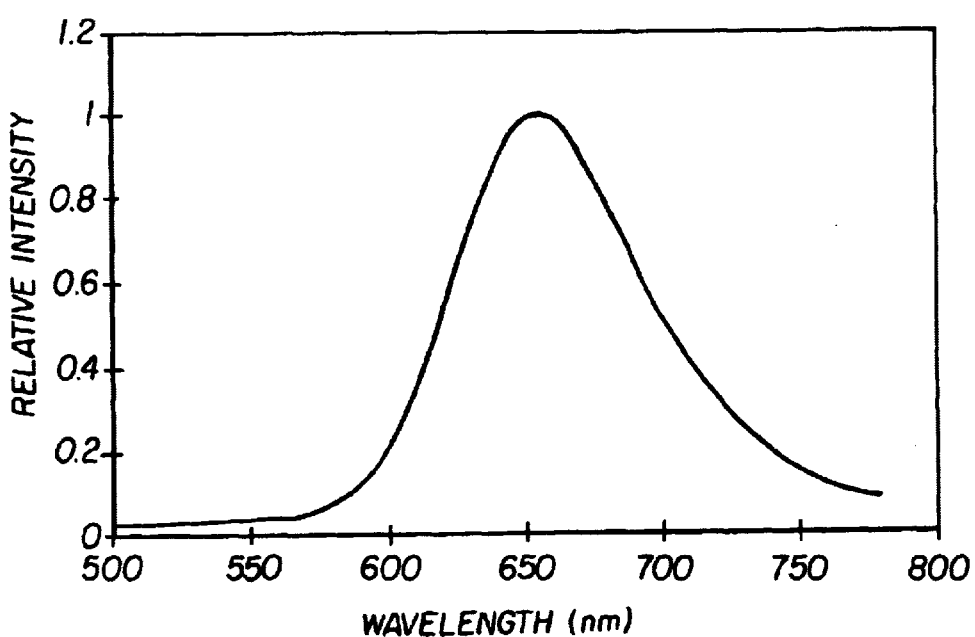
FIG. 3 shows the plot of the spectral characteristics of an EL device which uses the compound TJDCP (III-08) as a red dopant in accordance with the present invention.
Figure 4:
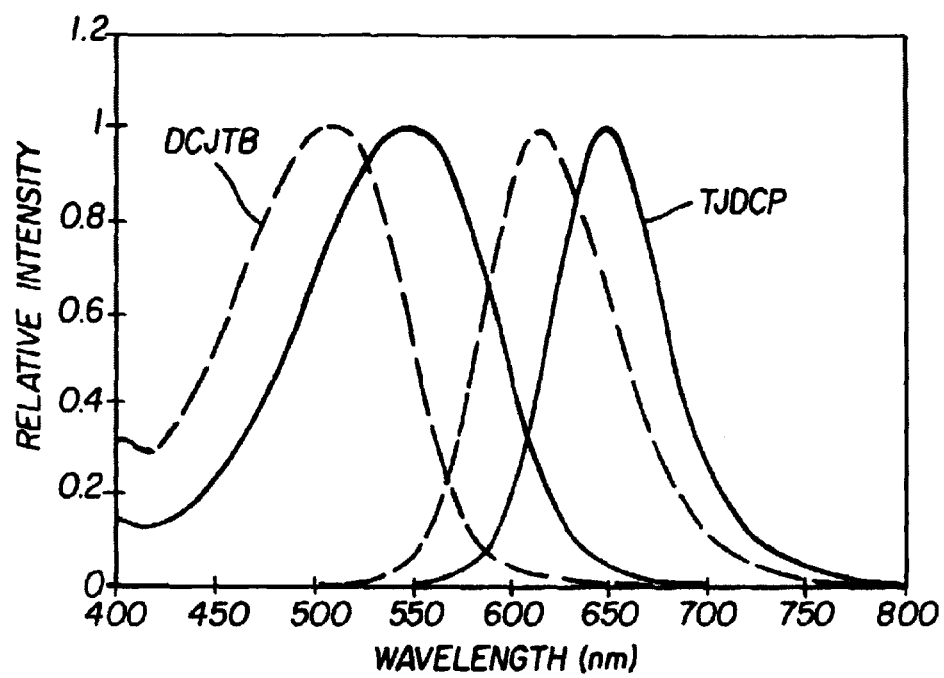
FIG. 4 shows the plot of the absorption and emission spectral characteristics of the compounds TJDCP (III-08) and DCJTB in accordance with the present invention.
Figure 5:
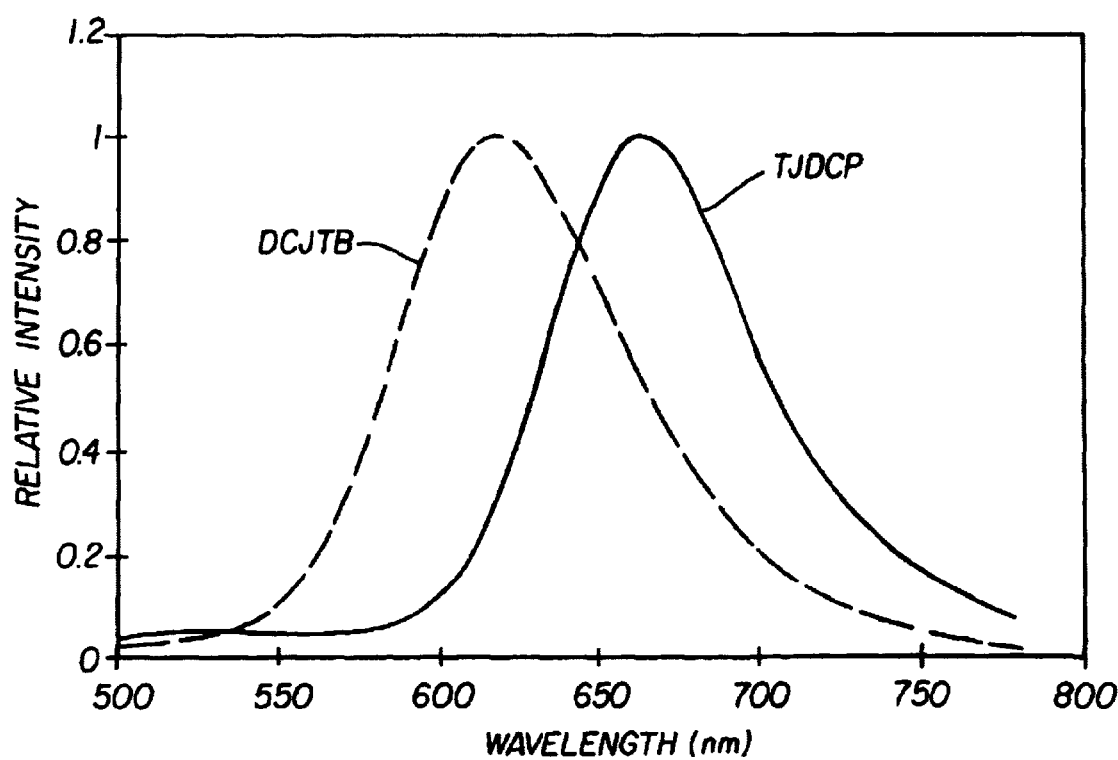
FIG. 5 shows the plot of the spectral characteristics comparison of EL devices which use the compounds TJDCP (III-08) and DCJTB as red dopant in accordance with the present invention.

An EL device 100 according to the invention is schematically illustrated in FIG. 1.

General Device Architecture

The present invention can be employed in most OLED device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with a thin film transistor (TFT).

There are numerous configurations of the organic layers wherein the present invention can be successfully practiced. A typical structure is shown in FIG. 1 and includes a substrate 101, a conductive anode layer 103, an optional hole-injecting layer 105, a hole-transporting layer 107, a light-emitting layer 109, an electron-transporting layer 111, and a cathode layer 113. These layers are described in detail below. Note that the substrate 101 may alternatively be located adjacent to the cathode layer 113, or the substrate 101 may actually constitute the anode or cathode. Also, the total combined thickness of the organic layers is preferably less than 500 nm.

Substrate

The substrate 101 can either be light transmissive or opaque, depending on the intended direction of light emission. The light transmissive property is desirable for viewing the EL emission through the substrate.

Transparent glass or plastic are commonly employed in such cases. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, ceramics, and circuit board materials. Of course it is necessary to provide in these device configurations a light-transparent top electrode.

Anode

The conductive anode layer 103 is commonly formed over the substrate and, when EL emission is viewed through the anode, should be transparent or substantially transparent to the emission of interest. Common transparent anode materials used in this invention are indium-tin oxide (ITO) and tin oxide, but other metal oxides can work including, but not limited to, aluminum- or indium-doped zinc oxide (IZO), magnesium-indium oxide, and nickel-tungsten oxide. In addition to these oxides, metal nitrides, such as gallium nitride, and metal selenides, such as zinc selenide, and metal sulfides, such as zinc sulfide, can be used in conductive anode layer 103. For applications where EL emission is viewed through the top electrode, the transmissive characteristics of conductive anode layer 103 are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes.

Hole-Injecting Layer (HIL)

While not always necessary, it is often useful that a hole-injecting layer 105 be provided between conductive anode layer 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in commonly-assigned U.S. Pat. No. 4,720,432, and plasma-deposited fluorocarbon polymers as described in commonly-assigned U.S. Pat. No. 6,208,075. Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al commonly-assigned U.S. Pat. Nos. 3,567,450 and 3,658,520.

A more preferred class of aromatic tertiary amines are those which include at least two aromatic tertiary amine moieties as described in commonly-assigned U.S. Pat. Nos. 4,720,432 and 5,061,569. Such compounds include those represented by structural formula (A).

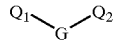

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

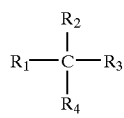

B where $R_1$ and $R_2$ each independently represents a hydrogen atom, an aryl group, or an alkyl group or $R_1$ and $R_2$ together represent the atoms completing a cycloalkyl group; and $R_3$ and $R_4$ each independently represents an aryl group, which is in turn substituted with a diaryl substituted amino group, as indicated by structural formula (C):

C wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula (D).

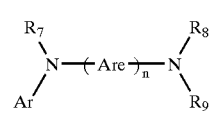

D wherein each Are is an independently selected arylene group, such as a phenylene or anthracene moiety, n is an integer of from 1 to 4, and Ar, $R_7$, $R_8$, and $R_9$ are independently selected aryl groups. In a typical embodiment, at least one of Ar, $R_7$, $R_8$, and $R_9$ is a polycyclic fused ring structure, e.g., a naphthalene.

The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
4,4'-Bis(diphenylamino)quadriphenyl
Bis(4-dimethylamino-2-methylphenyl)-phenylmethane
N,N,N-Tri(p-tolyl)amine
4-(di-p-tolylamino)-4'-[4(di-p-tolylamino)-styryl]stilbene
N,N,N',N'-Tetra-p-tolyl-4-4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl
4,4'-Bis[N-(1-naphthyl)-N-(2-naphthyl)amino]biphenyl 4,4"-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4"-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis{N-phenyl-N-[4-(1-naphthyl)-phenyl]amino}biphenyl
4,4'-Bis[N-phenyl-N-(2-pyrenyl)amino]biphenyl
2,6-Bis[N,N-di(2-naphthyl)amine]fluorene
1,5-Bis[N-(1-naphthyl)-N-phenylamino]naphthalene Another class of useful hole-transporting materials includes polycyclic aromatic compounds as described in commonly-assigned pending U.S. patent application Ser. No. 09/207,703, now U.S. Pat. No. 6,361,886, the disclosure of which is incorporated herein. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Light-Emitting Layer (LEL)

As more fully described in U.S. Pat. Nos. 4,769,292 and 5,935,721, the light-emitting layer (LEL) 109 of the organic EL element comprises a luminescent or fluorescent material where electroluminescence is produced as a result of electron-hole pair recombination in this region. The light-emitting layer can be comprised of a single material, but more commonly consists of a host material doped with a guest compound or compounds where light emission comes primarily from the dopant and can be of any color. The host materials in the light-emitting layer can be an electron-transporting material, as defined below, a hole-transporting material, as defined above, or another material or combination of materials that support hole-electron recombination. The dopant is usually chosen from highly fluorescent dyes, but phosphorescent compounds, e.g., transition metal complexes as described in WO 98/55561, WO 00/18851, WO 00/57676, and WO 00/70655 are also useful. Dopants are typically coated as 0.01 to 10% by weight into the host material.

An important relationship for choosing a dye as a dopant is a comparison of the bandgap potential which is defined as the energy difference between the highest occupied molecular orbital and the lowest unoccupied molecular orbital of the molecule. For efficient energy transfer from the host to the dopant molecule, a necessary condition is that the band gap of the dopant is smaller than that of the host material.

Host and emitting molecules known to be of use include, but are not limited to, those disclosed in U.S. Pat. Nos. 4,768,292; 5,141,671; 5,150,006; 5,151,629; 5,405,709; 5,484,922; 5,593,788; 5,645,948; 5,683,823; 5,755,999; 5,928,802; 5,935,720; 5,935,721; and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

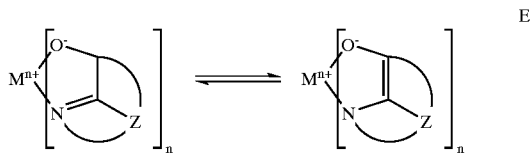

E wherein

M represents a metal;

n is an integer of from 1 to 4; and

Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]

CO-2: Magnesium bisoxine [alias, bis(8-quinolinolato)magnesium(II)]

CO-3: Bis[benzo{f}-8-quinolinolato]zinc(II)

CO-4: Bis(2-methyl-8-quinolinolato)aluminum(III)-μ-oxo-bis(2-methyl-8-quinolinolato)aluminum(III)

CO-5: Indium trisoxine [alias, tris(8-quinolinolato)indium]

CO-6: Aluminum tris(5-methyloxine)[alias, tris(5-methyl-8-quinolinolato)aluminum(III)]

CO-7: Lithium oxine [alias, (8-quinolinolato)lithium(I)]

CO-8: Gallium oxine [alias, tris(8-quinolinolato)gallium(III)]

CO-9: Zirconium oxine [alias, tetra(8-quinolinolato)zirconium(IV)]

Derivatives of 9,10-di-(2-naphthyl)anthracene (Formula F) constitute one class of useful hosts capable of supporting electroluminescence, and are particularly suitable for light emission of wavelengths longer than 400 nm, e.g., blue, green, yellow, orange or red.

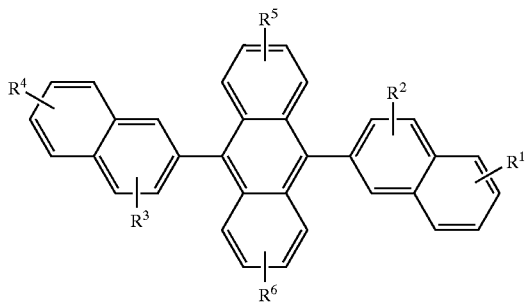

F wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;
Group 2: aryl or substituted aryl of from 5 to 20 carbon atoms;
Group 3: carbon atoms from 4 to 24 necessary to complete a fused aromatic ring of anthracenyl; pyrenyl, or perylenyl;
Group 4: heteroaryl or substituted heteroaryl of from 5 to 24 carbon atoms as necessary to complete a fused heteroaromatic ring of furyl, thienyl, pyridyl, quinolinyl or other heterocyclic systems;
Group 5: alkoxylamino, alkylamino, or arylamino of from 1 to 24 carbon atoms; and
Group 6: fluorine, chlorine, bromine or cyano.

Illustrative examples include 9,10-di-(2-naphthyl) anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene.

Benzazole derivatives (Formula G) constitute another class of useful hosts capable of supporting electroluminescence, and are particularly suitable for light emission of wavelengths longer than 400 nm, e.g., blue, green, yellow, orange or red.

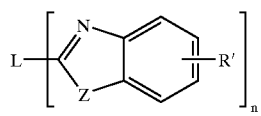

G

Where:
N is an integer of 3 to 8;
Z is O, NR or S; and
R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring;

L is a linkage unit consisting of alkyl, aryl, substituted alkyl, or substituted aryl, which conjugately or unconjugately connects the multiple benzazoles together.

An example of a useful benzazole is 2,2',2"-(1,3,5-phenylene)tris[1-phenyl-1H-benzimidazole] (TPBI).

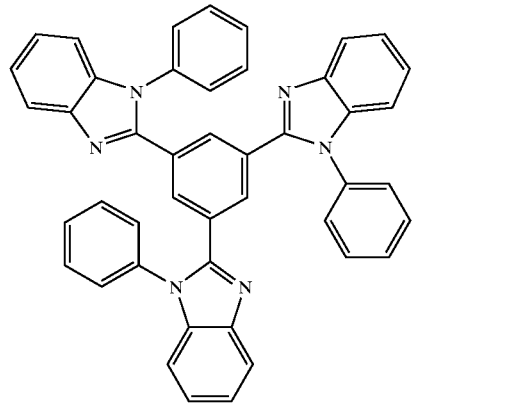

TPBI

Organic device shown in FIG. 1 is illustrative of preferred embodiment of the present invention. The light-emitting layer (LEL) 109 of the organic EL element comprises a luminescent or fluorescent material where electroluminescence is produced as a result of electron-hole pair recombination in this region. One particular organic luminescent medium containing a compound of the formula:

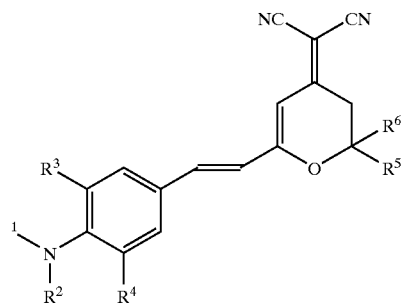

wherein:
R1, and R2 are individually alkyl of from 1 to 20 carbon atoms, aryl, substituted aryl, carbocyclic and other heterocyclic systems; and R1, and R2 can be connected to form 5 or 6 member ring systems; and R3, and R4 are individually hydrogen; alkyl of from 1 to 10 carbon atoms, and a branched or unbranched 5 or 6 member substituent ring connecting with R1, R2 respectively; and R5 and R6 are individually hydrogen; alkyl of from 1 to 20 carbon atoms; aryl and heteroaryl of from 5 to 24 carbon atoms; and R6 can be connected with R5 to form a branched or unbranched 5 or 6 member carbocyclic ring.

In EL devices the following compound structure has been found to be particularly effective. Illustrative examples of useful dopants include, but are not limited to, the following:

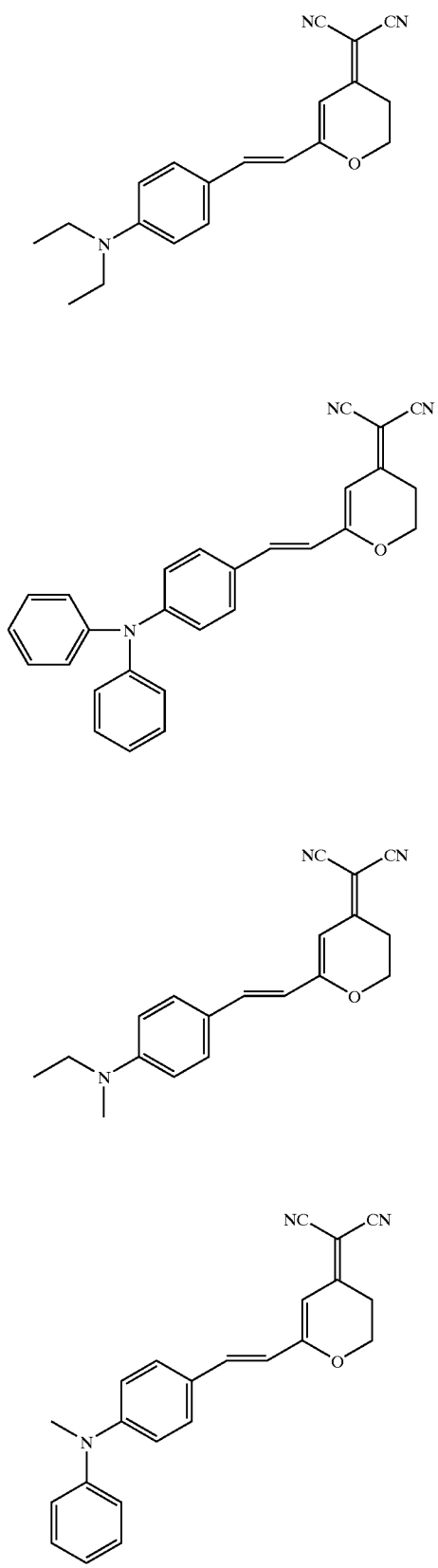
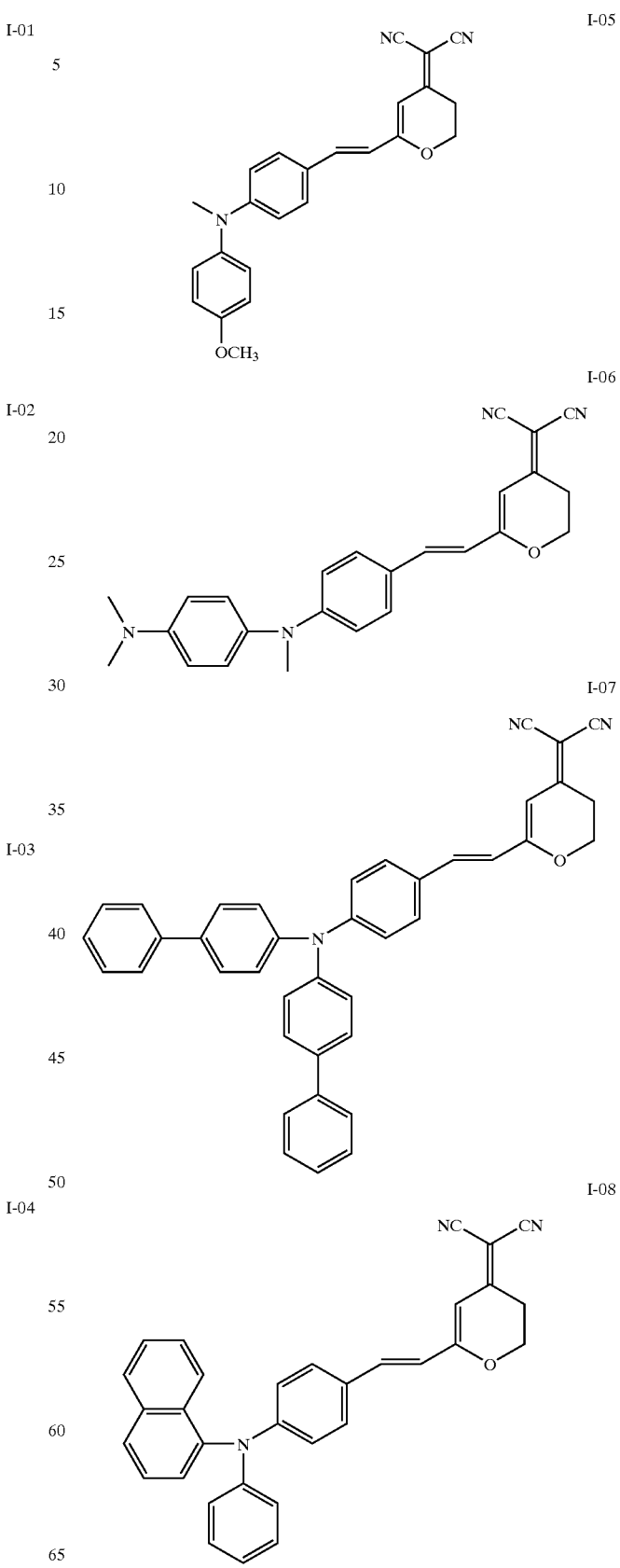

-continued
I-09
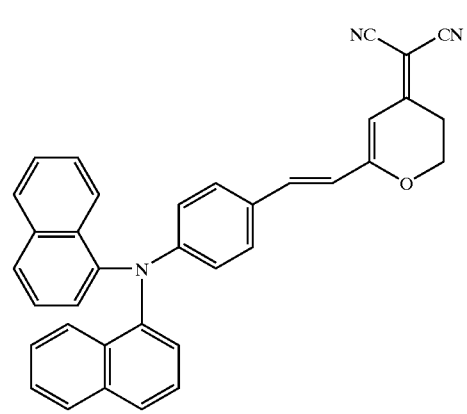
I-10
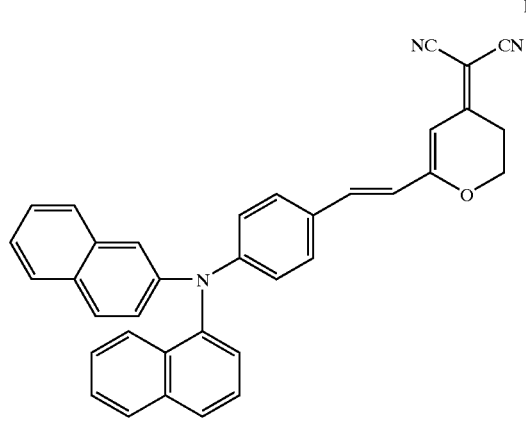
I-11
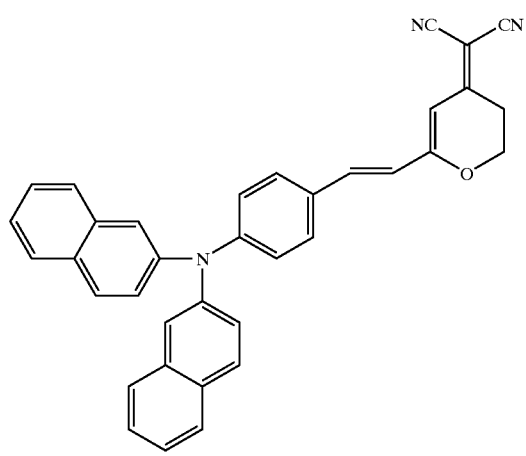
I-12
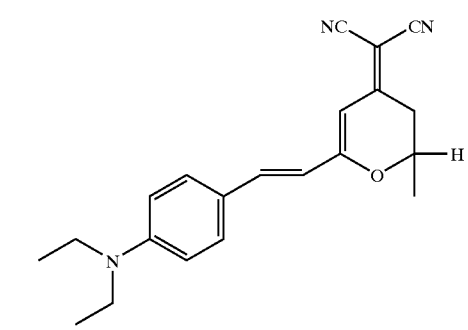
-continued
I-13
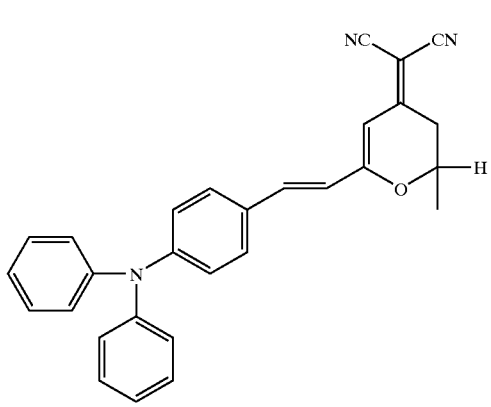
I-14
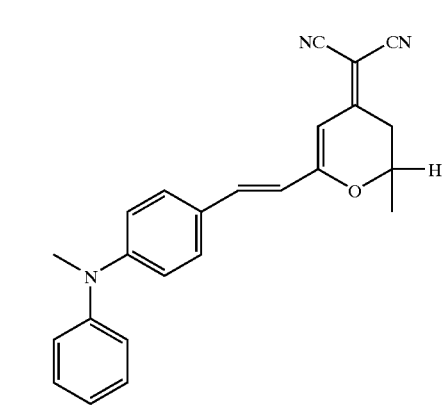
I-15
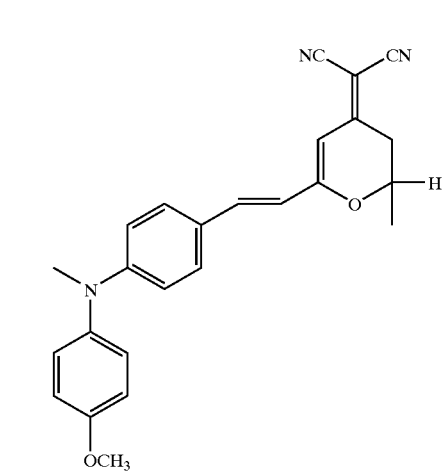
I-16
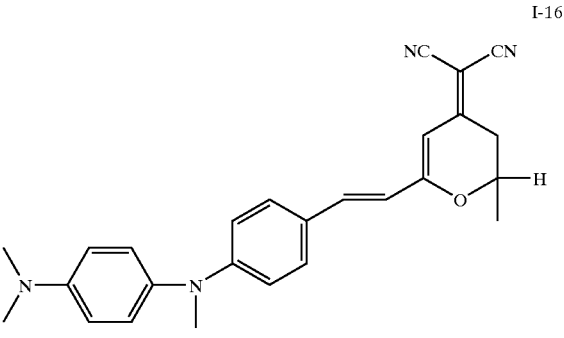

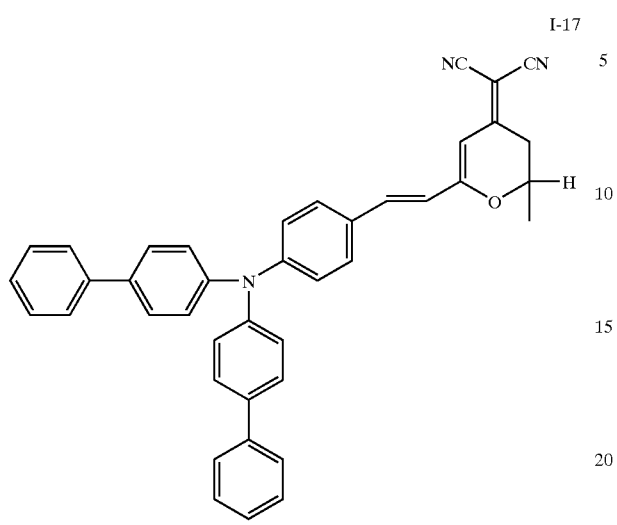
I-17
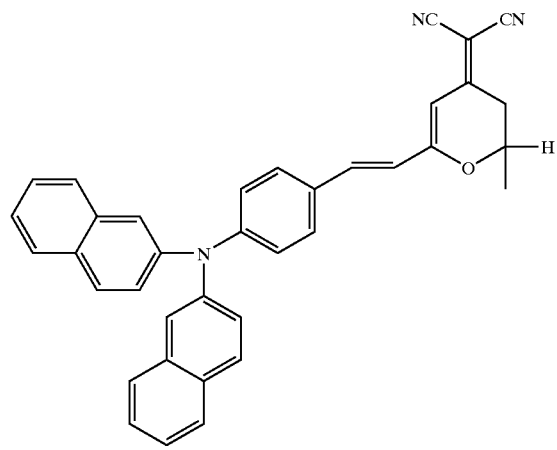
I-20
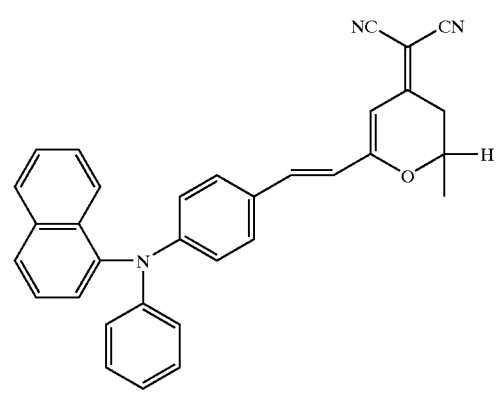
I-18
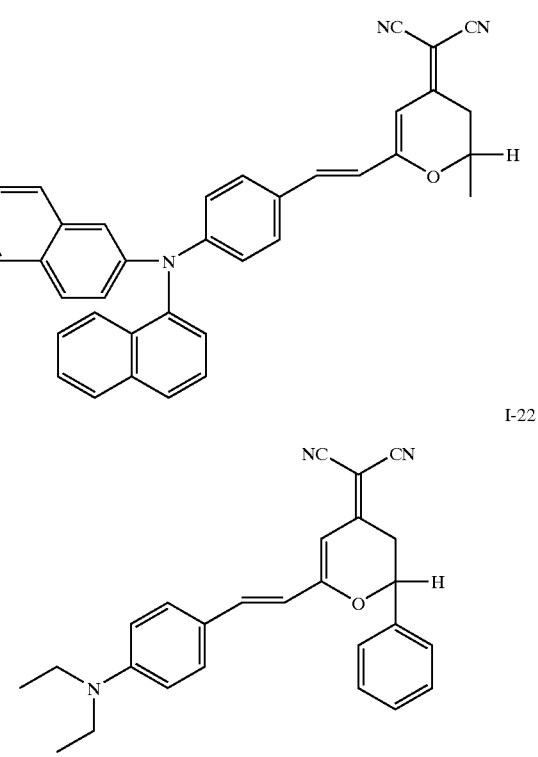
I-21
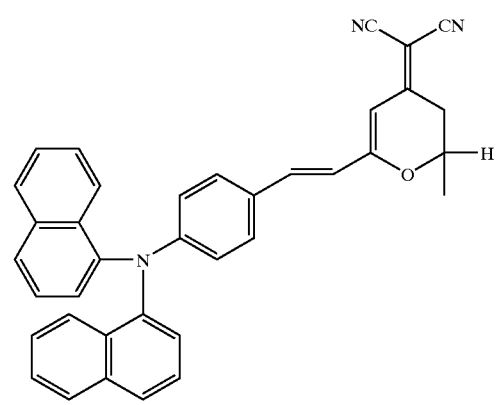
I-19
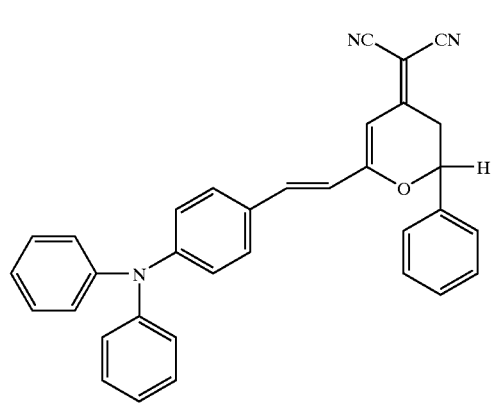
I-22
I-23

I-24
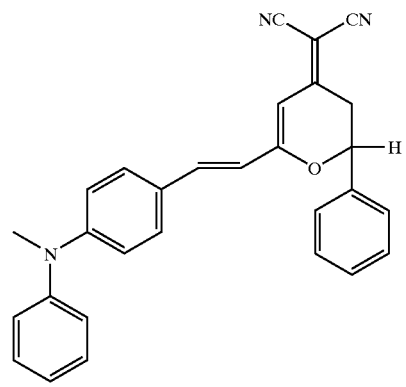
I-25
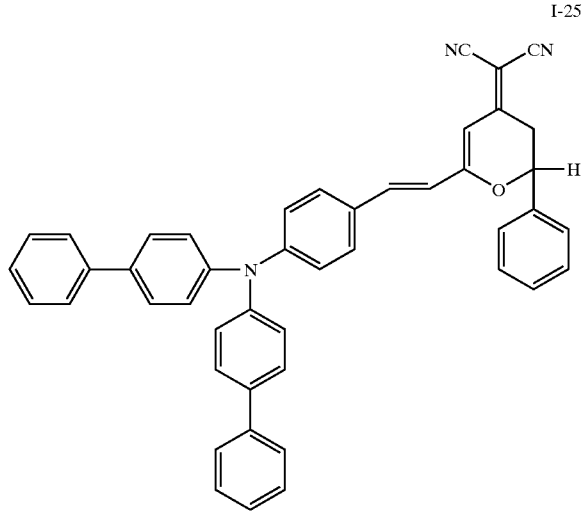
I-26
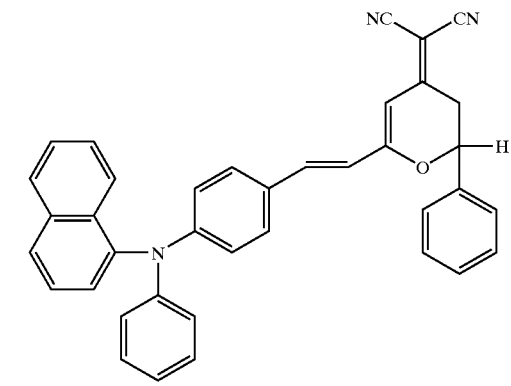
I-27
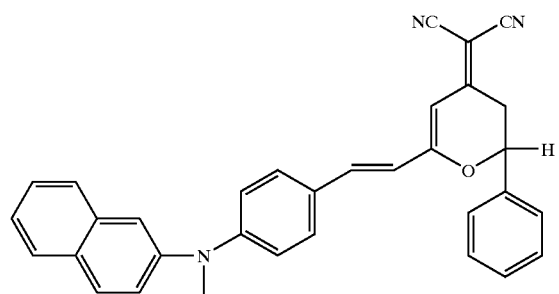
I-28
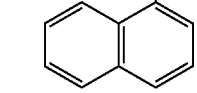
I-29
I-30

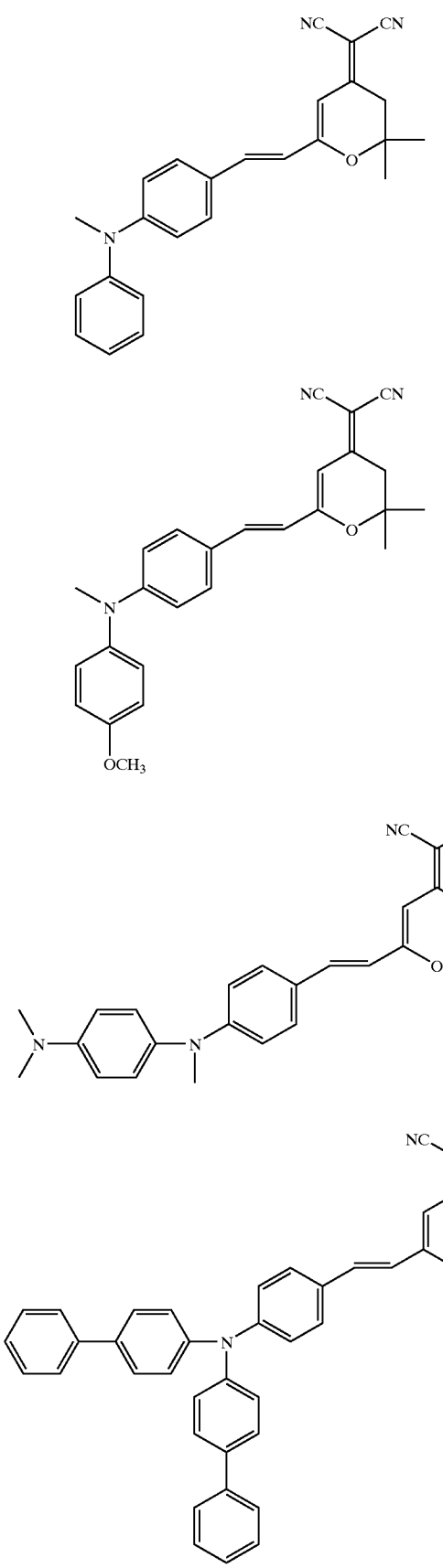
I-31
I-32
I-33
I-34
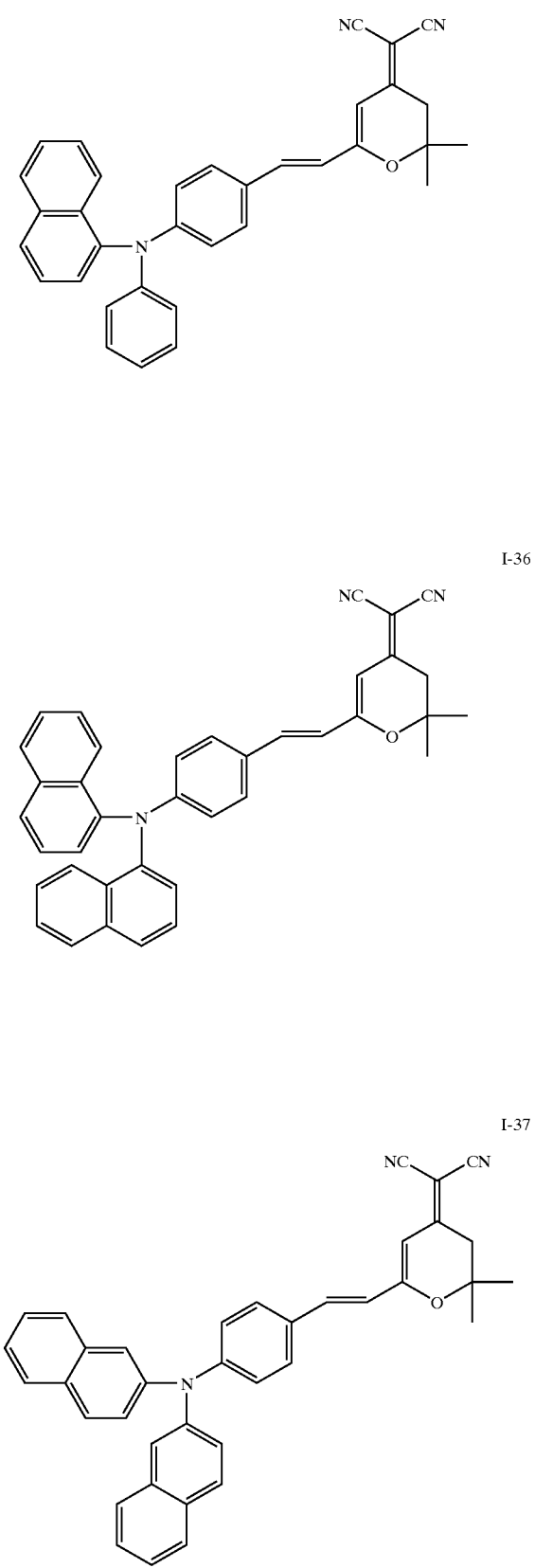
I-35
I-36
I-37

I-38
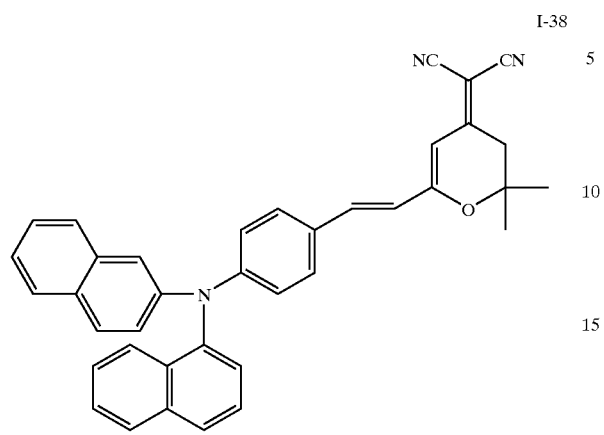
I-39
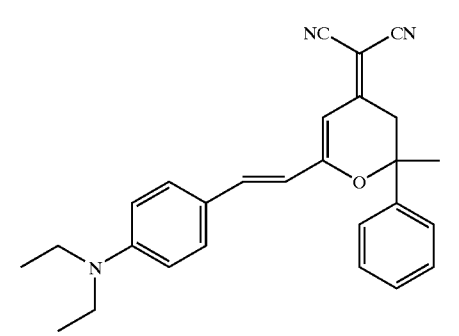
I-40
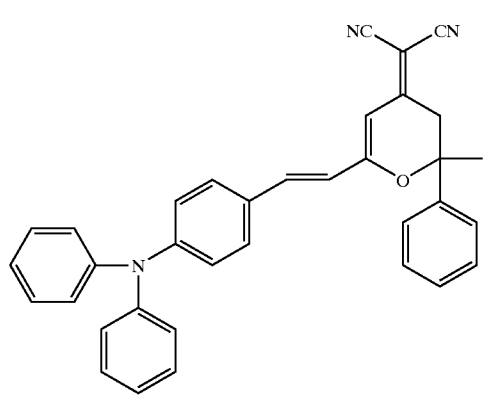
I-41
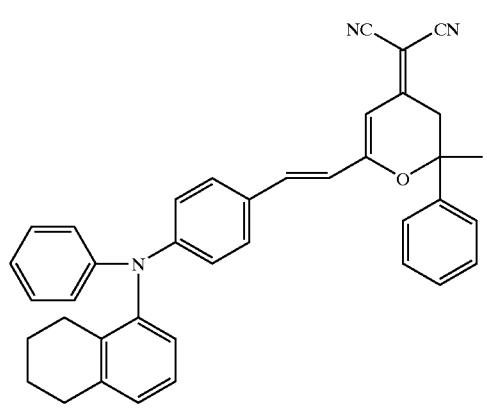
I-42
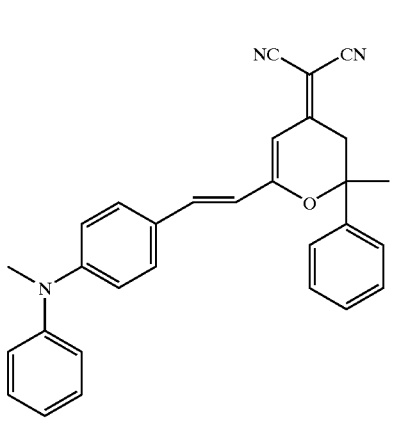
I-43
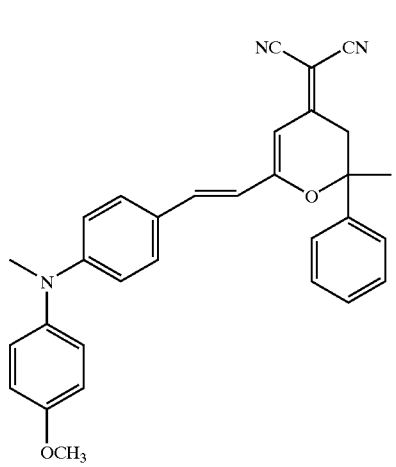
I-44
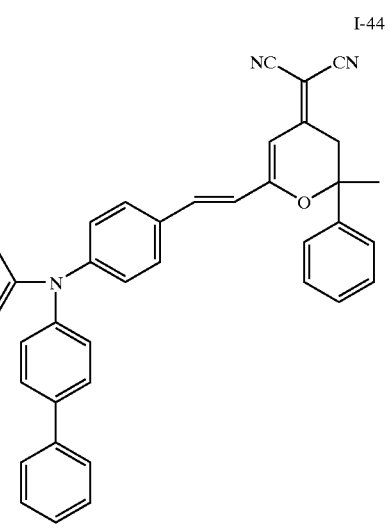

I-45
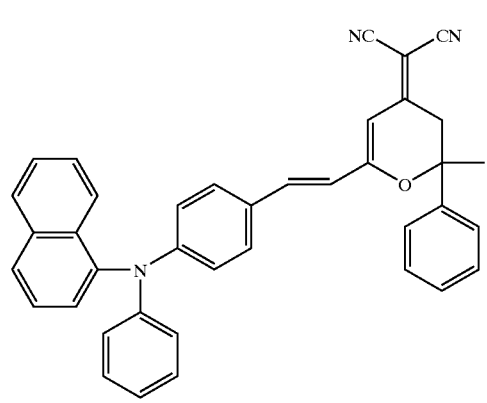
I-46
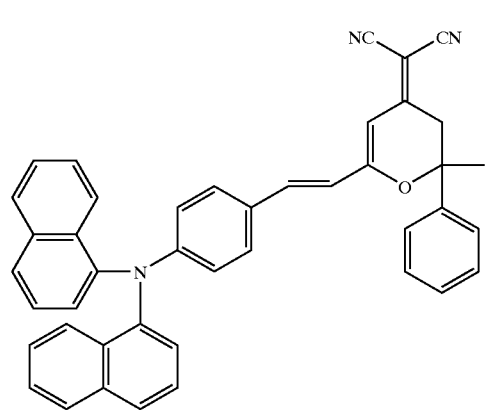
I-47
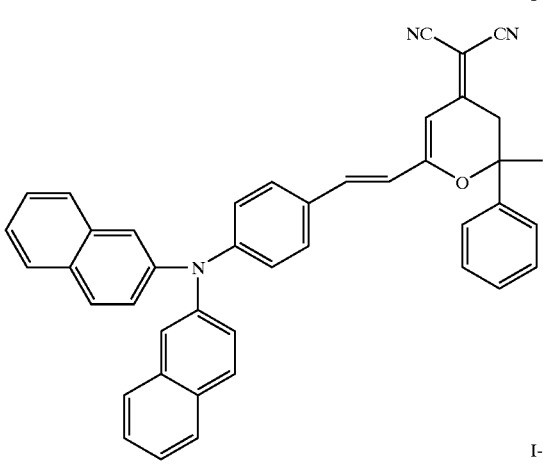
I-48
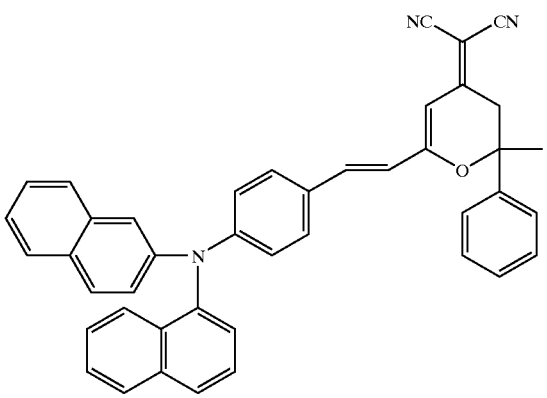
I-49
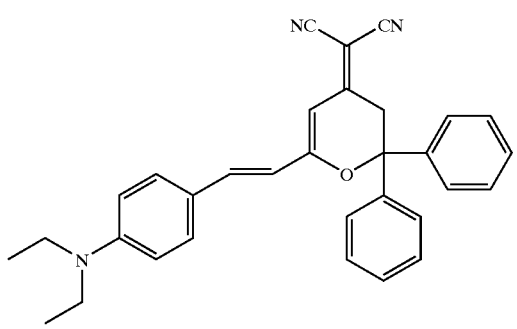
I-50
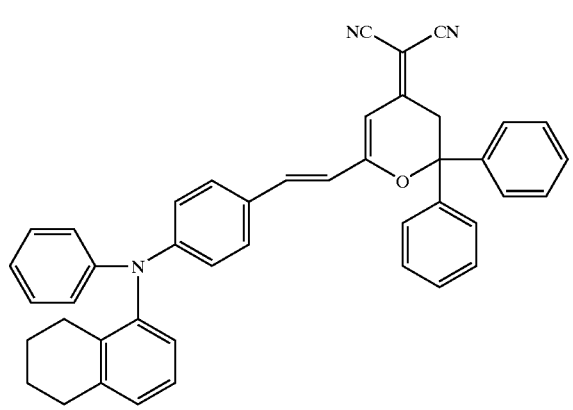
I-51
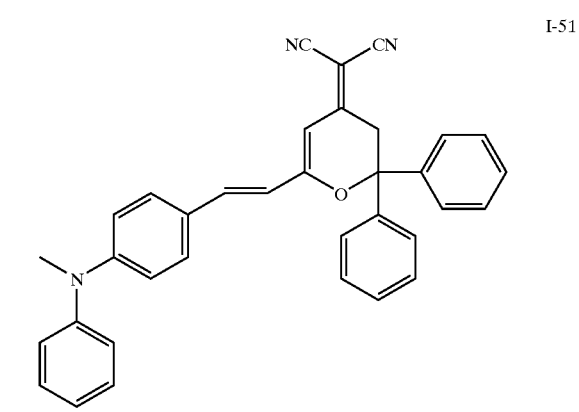
I-52
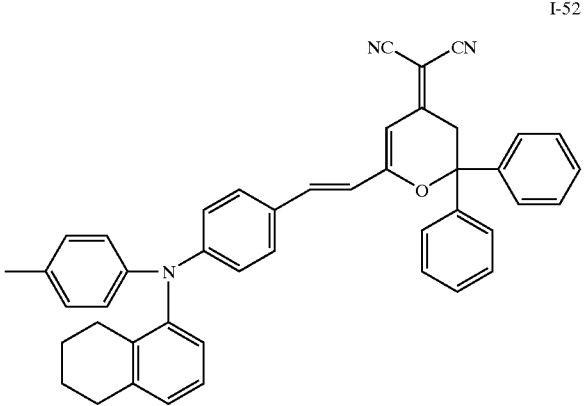

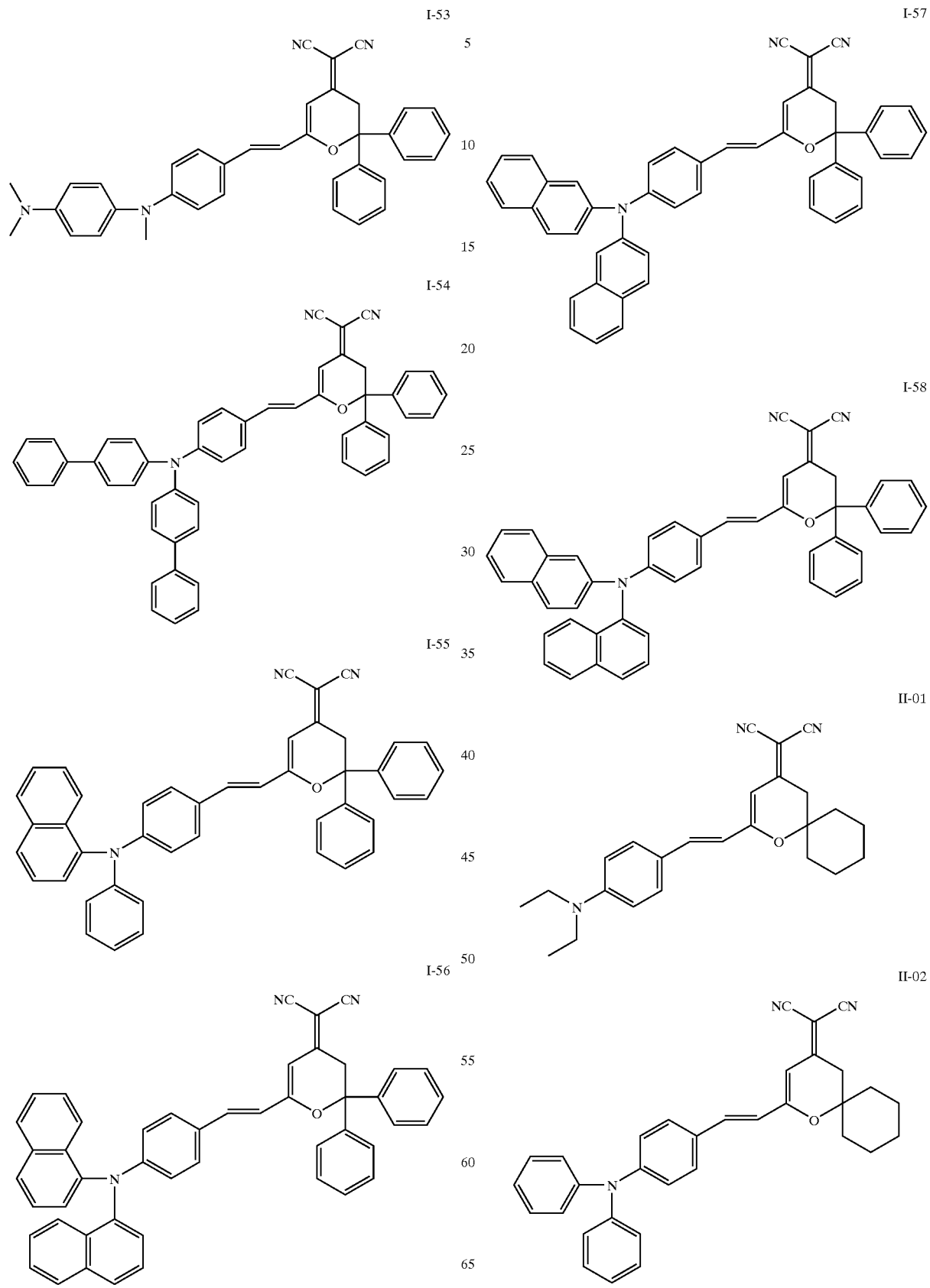

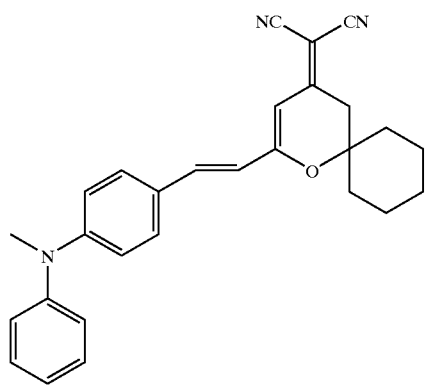
II-03
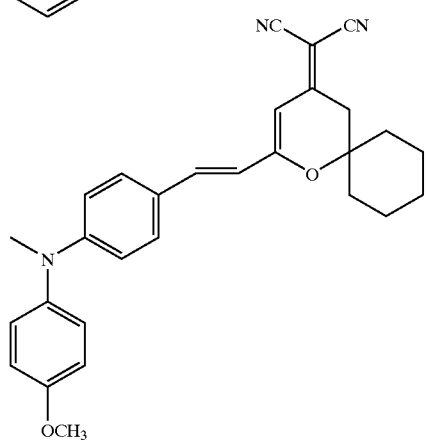
II-04
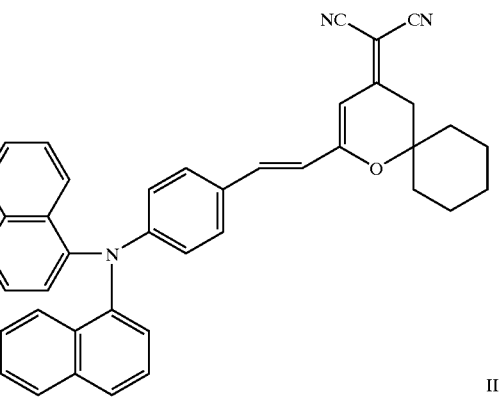
II-05
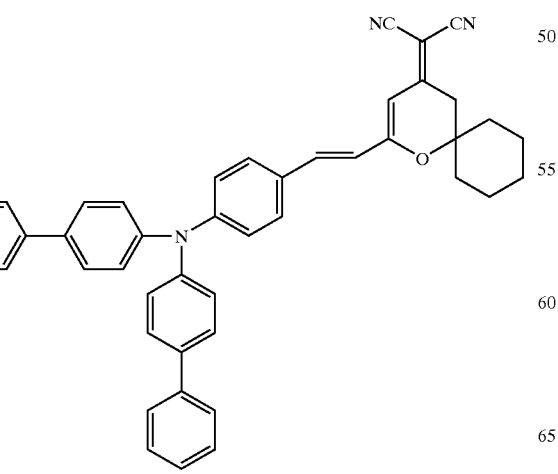
II-06
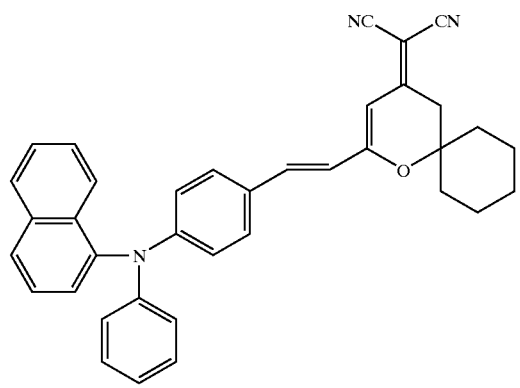
II-07
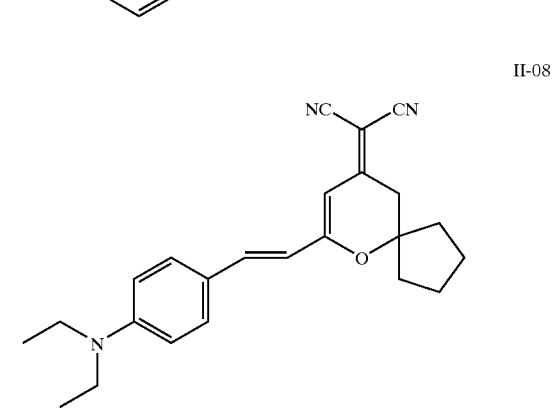
II-08
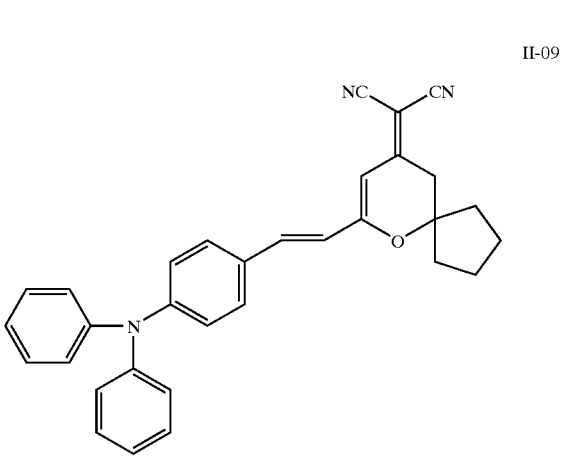
II-09
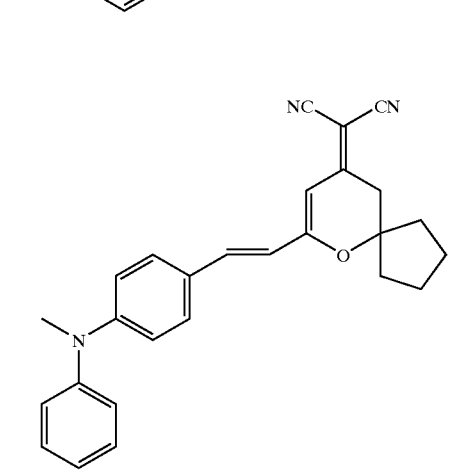
II-10

-continued
II-11
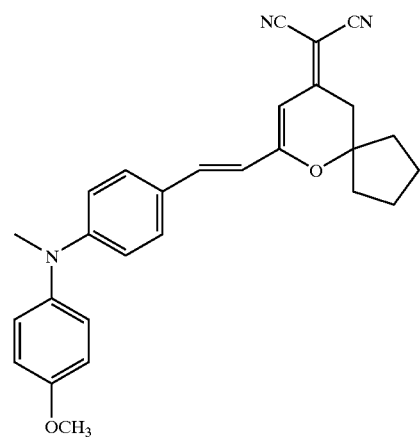
II-15
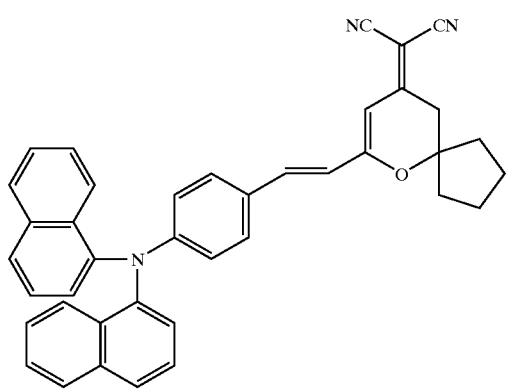
II-12
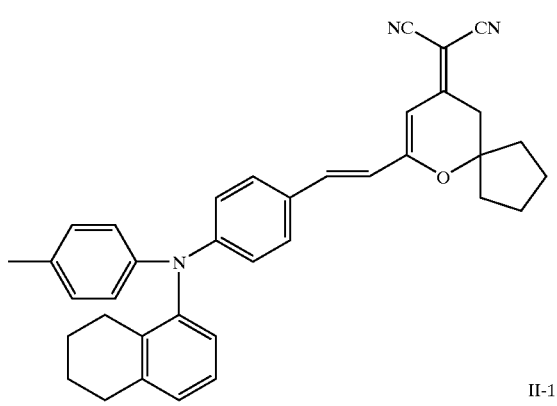
II-16
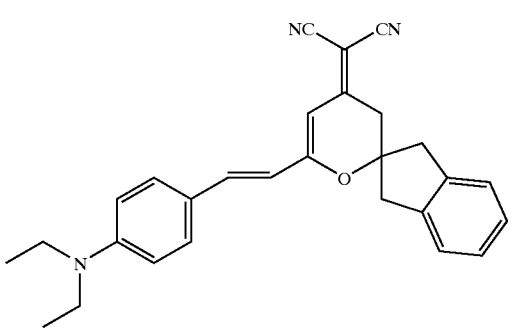
II-13
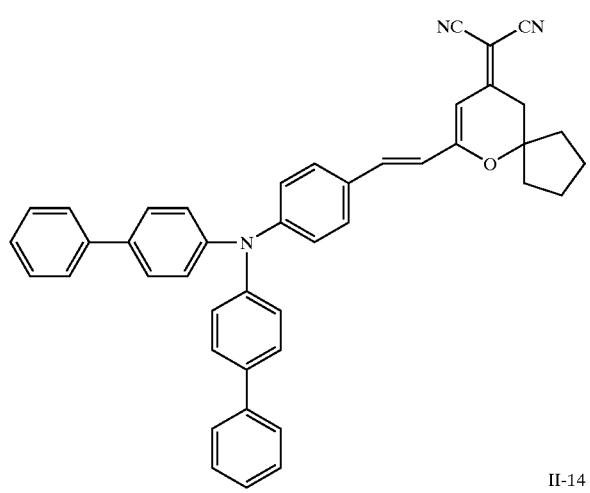
II-17
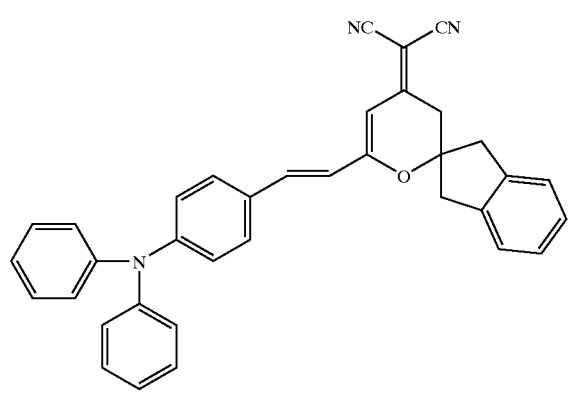
II-14
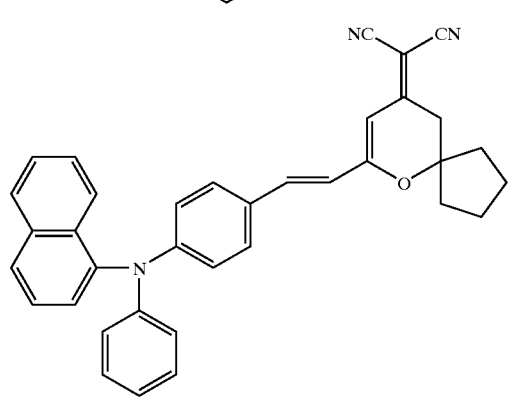
II-18
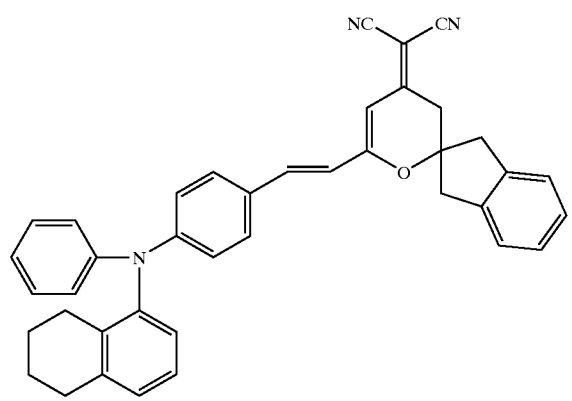

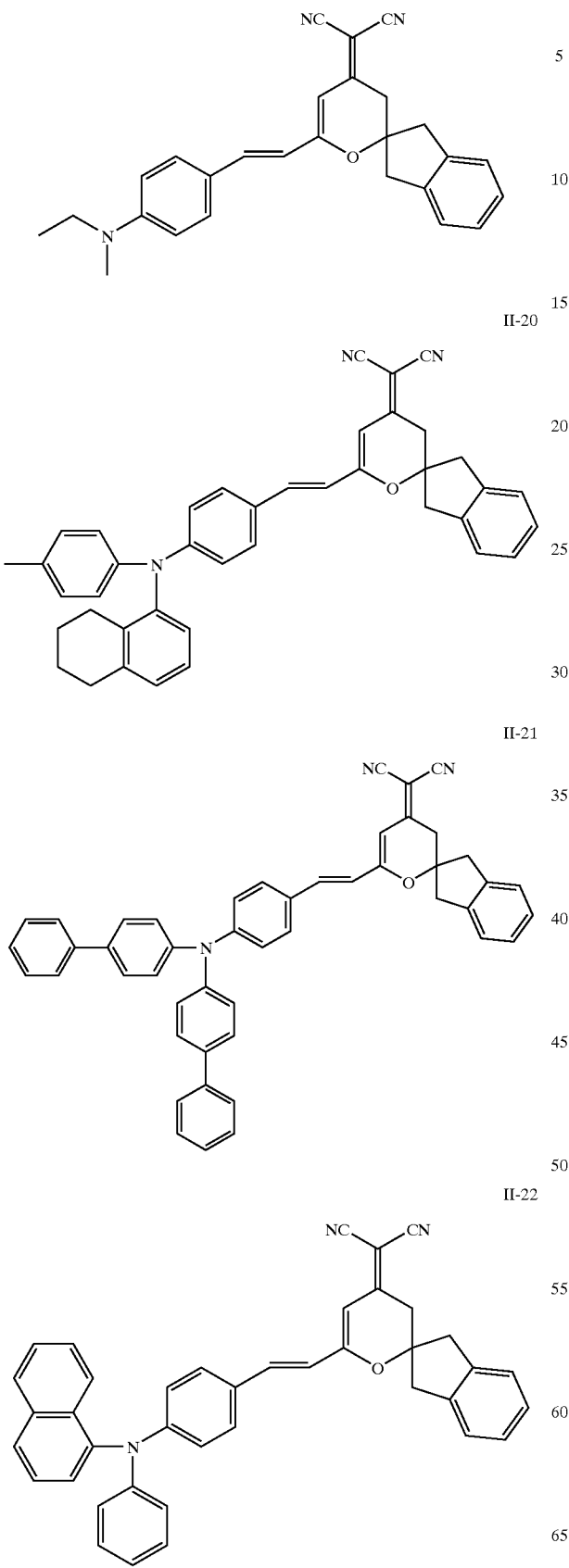
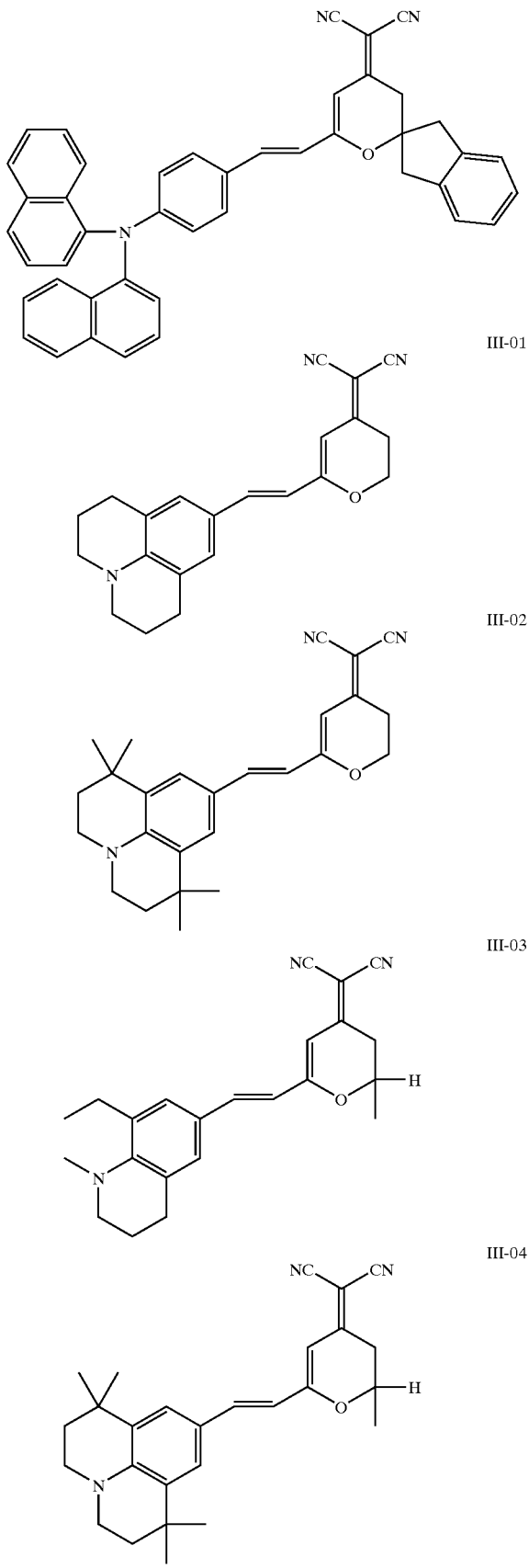

III-05
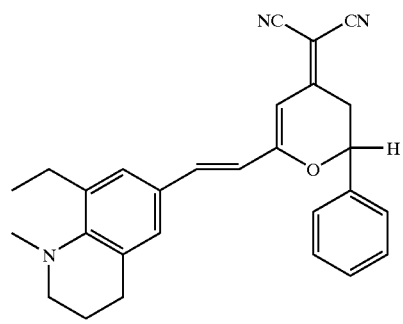
III-06
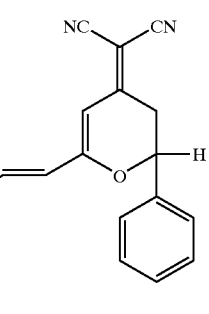
III-07
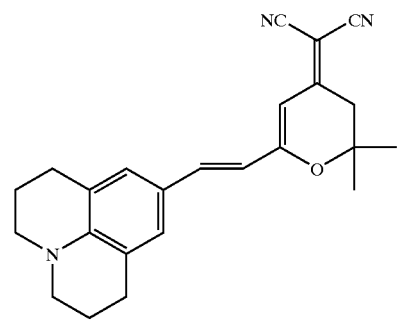
III-08
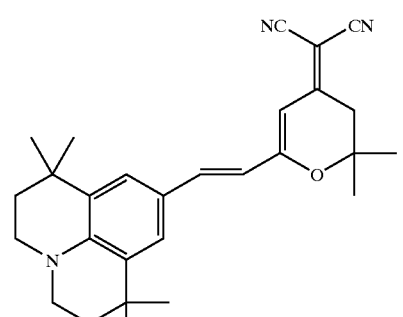
(See FIGS. 2–5)
III-09
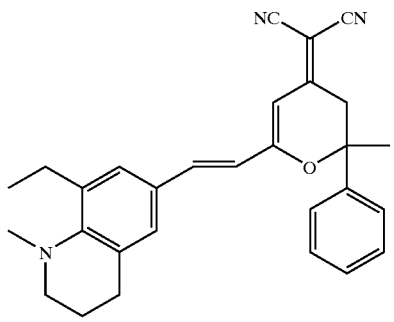
III-10
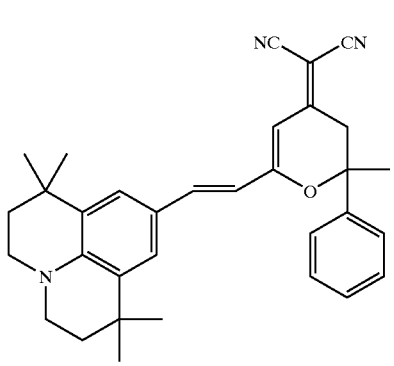
III-11
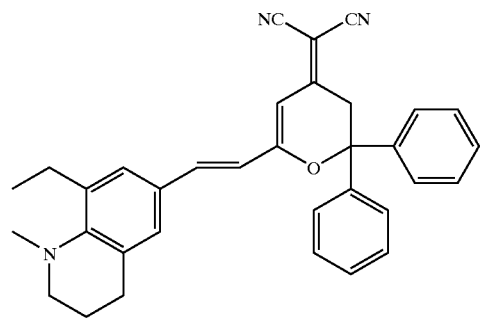
III-12
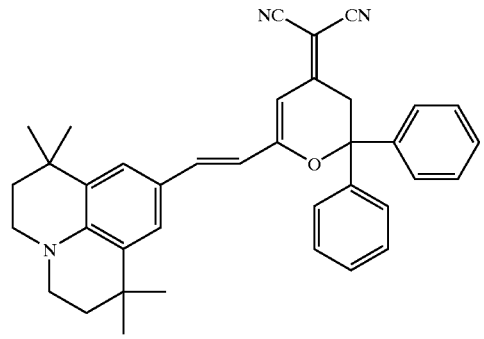

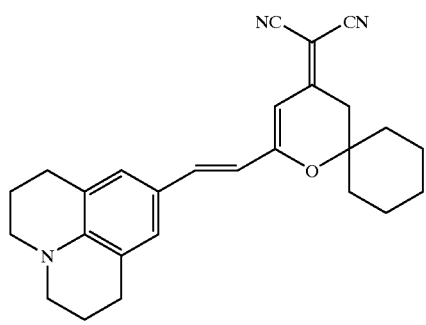 III-13
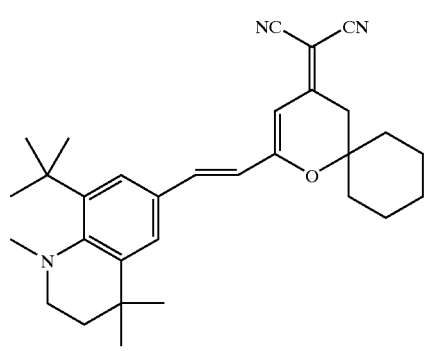 III-14
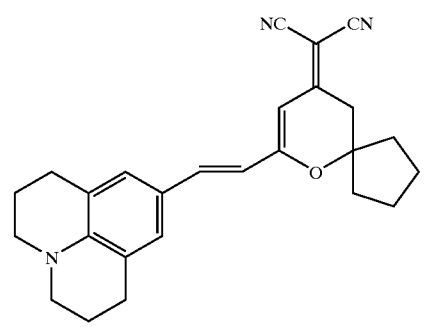 III-15
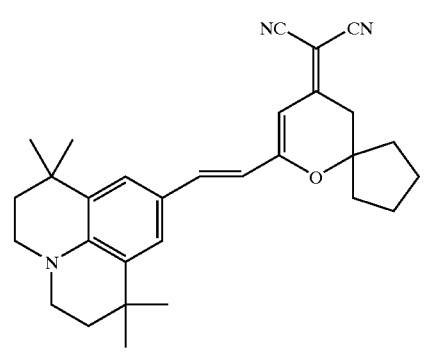 III-16
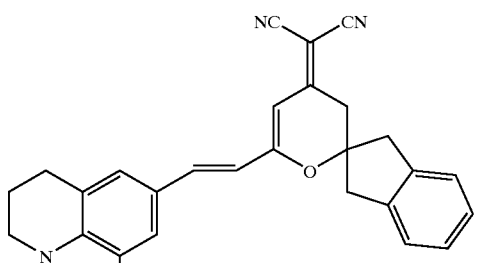 III-17
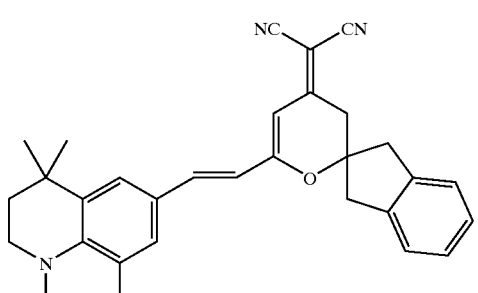 III-18
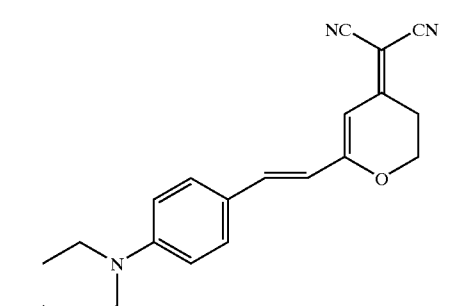 IV-01
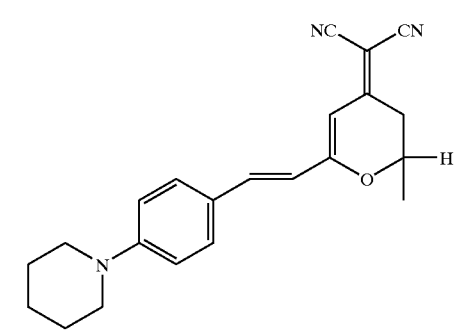 IV-02
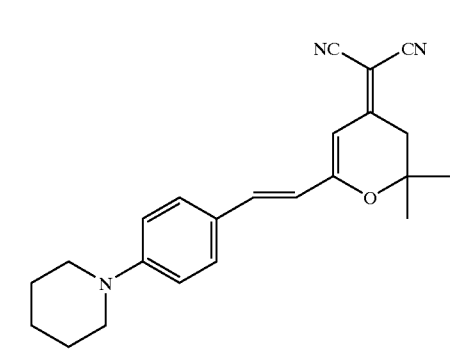 IV-03

IV-04
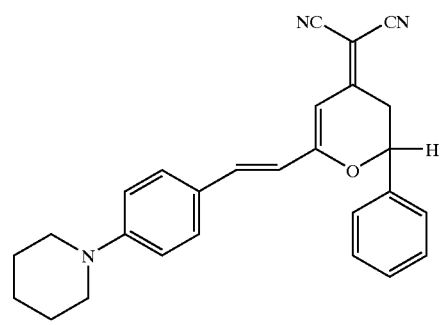
IV-05
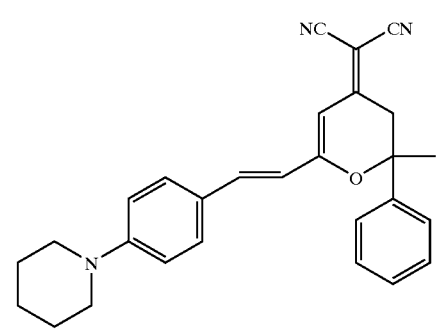
IV-06
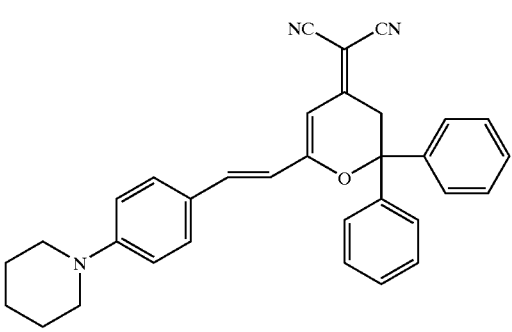
IV-07
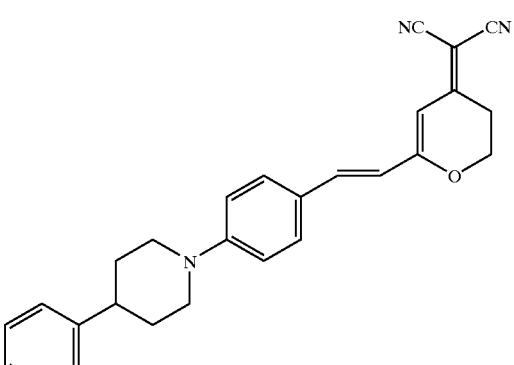
IV-08
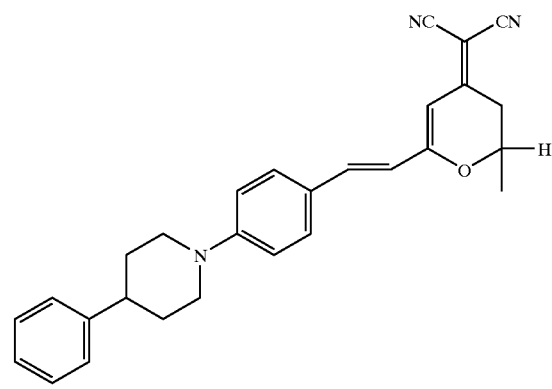
IV-09
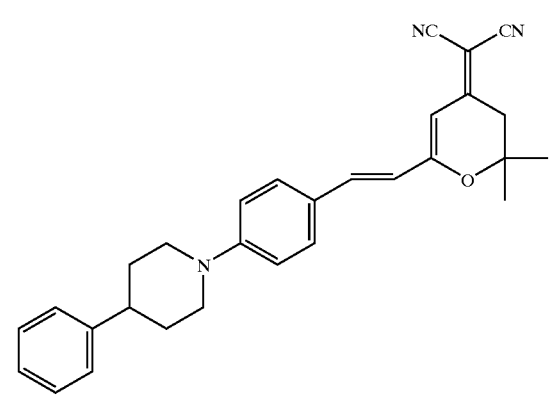
IV-10
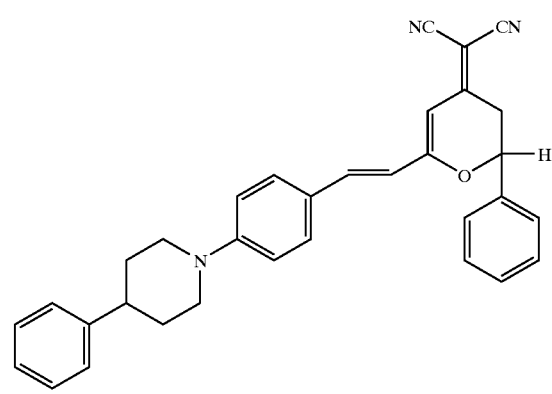
IV-11
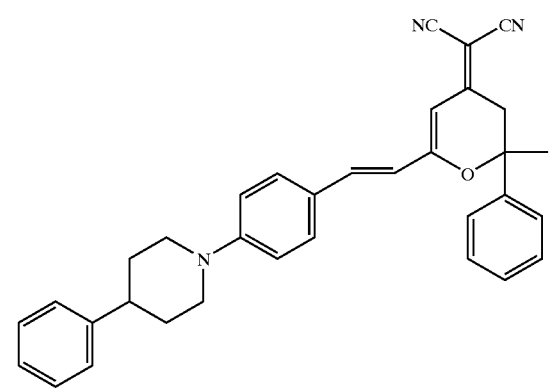

IV-12
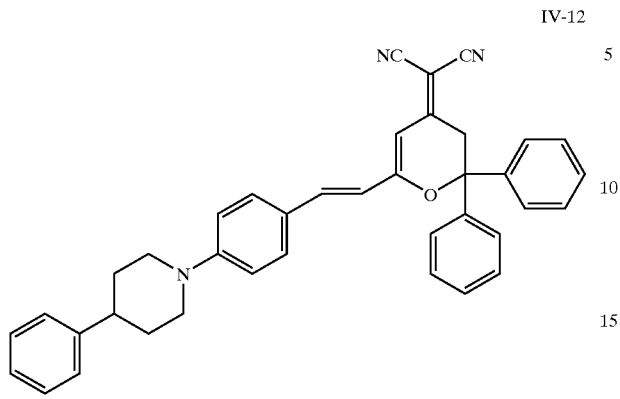
IV-16
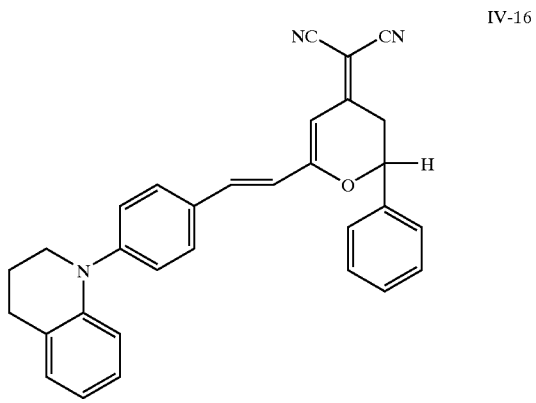
IV-13
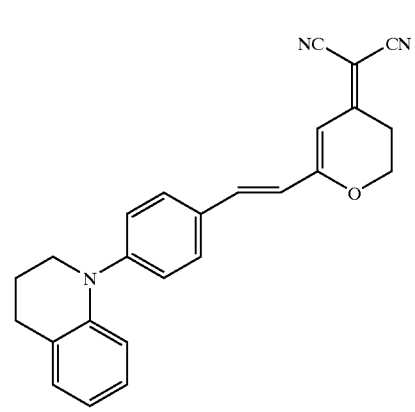
IV-17
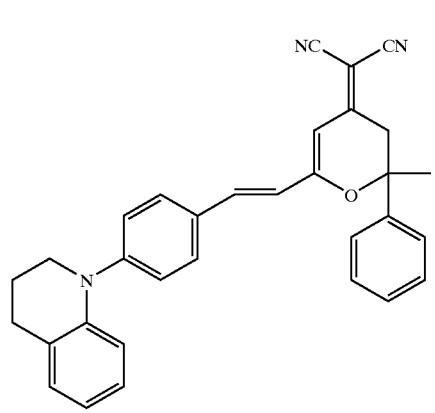
IV-14
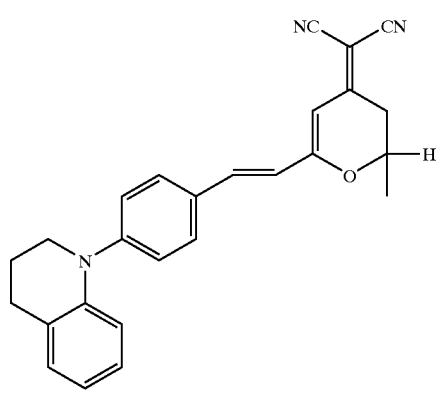
IV-18
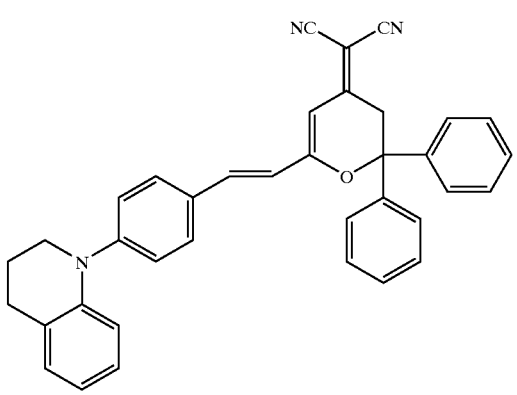
IV-15
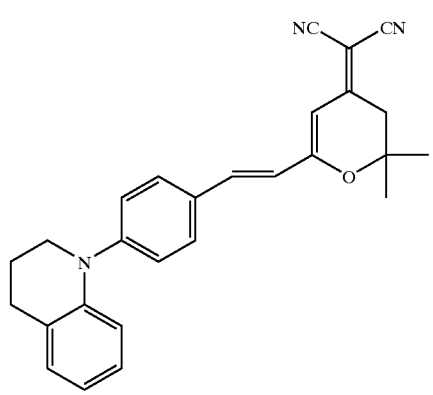
IV-19
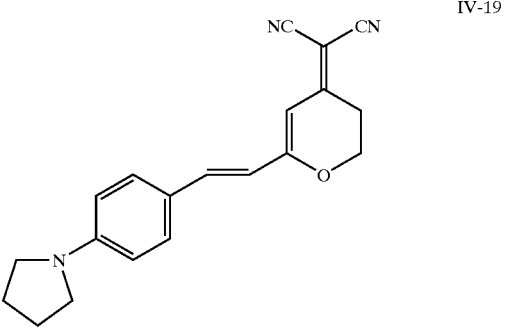

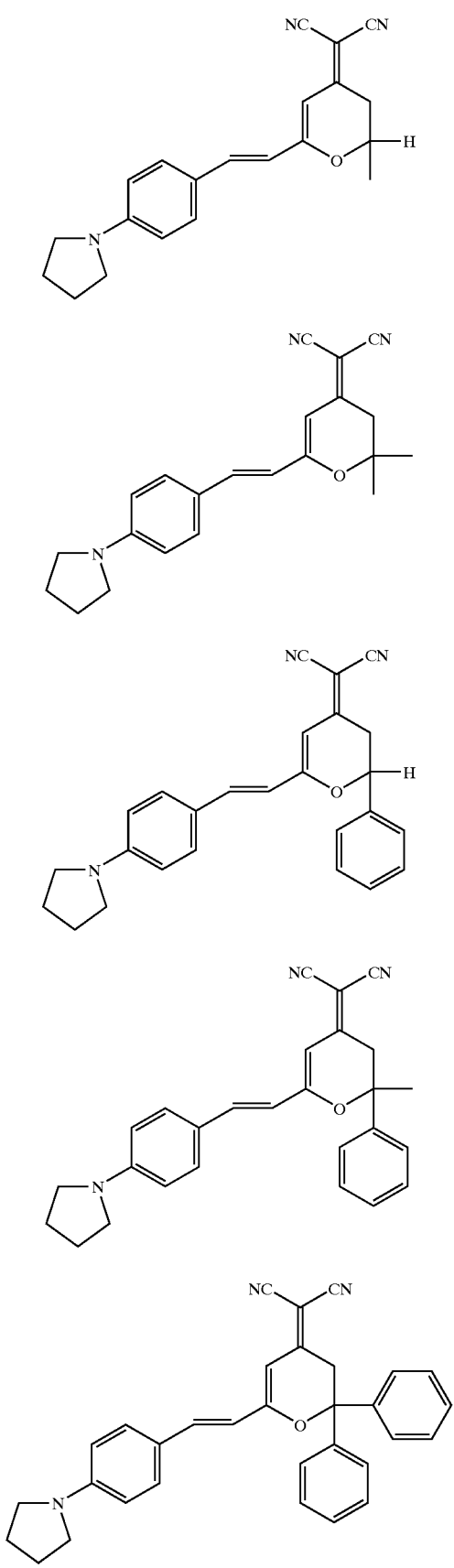
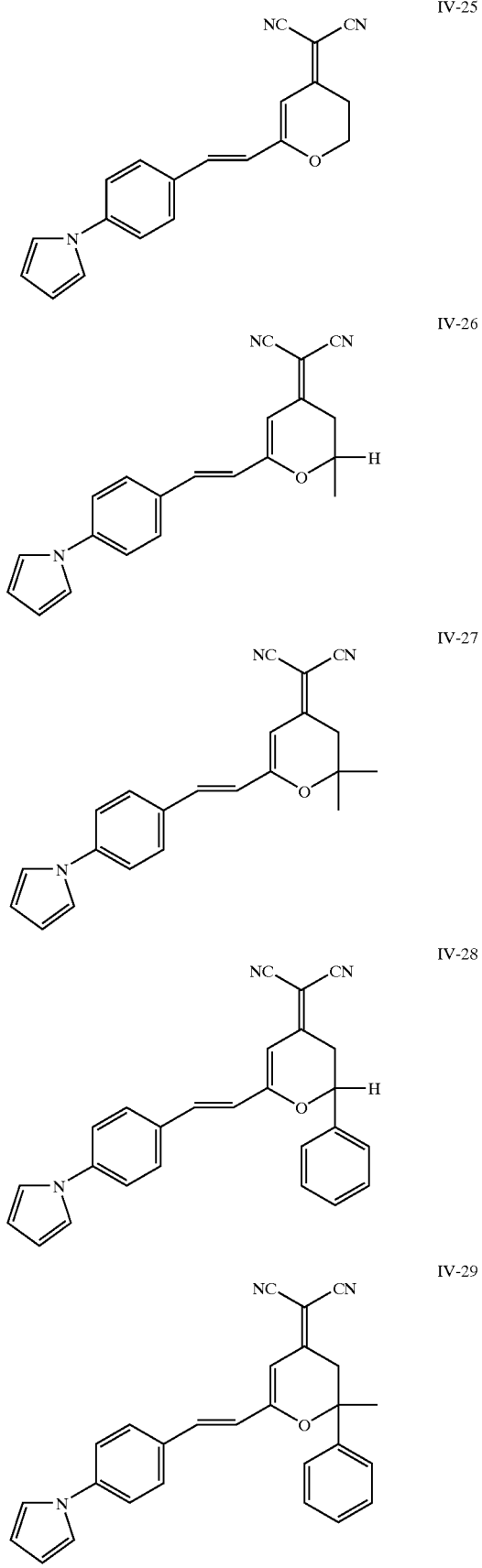

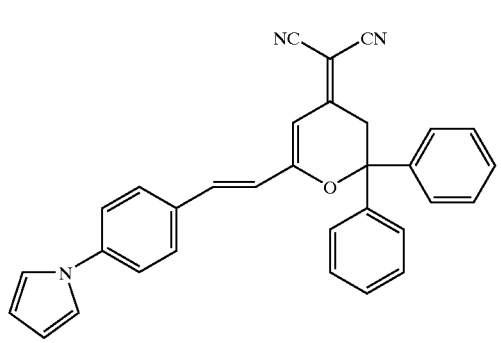
IV-30
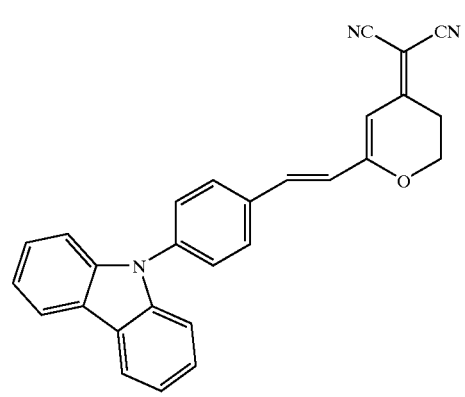
IV-31
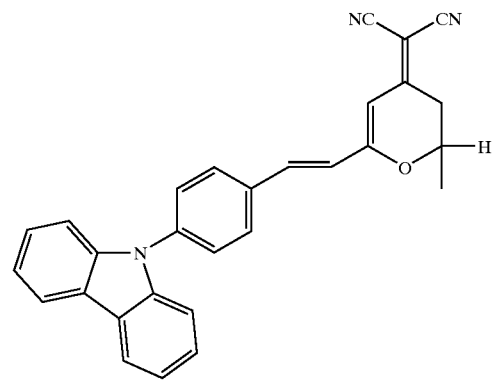
IV-32
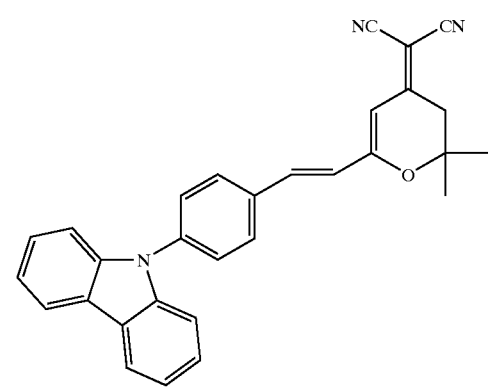
IV-33
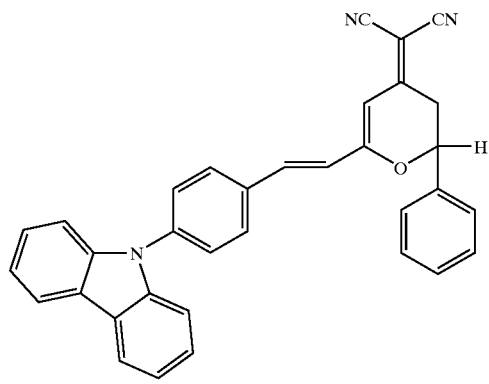
IV-34
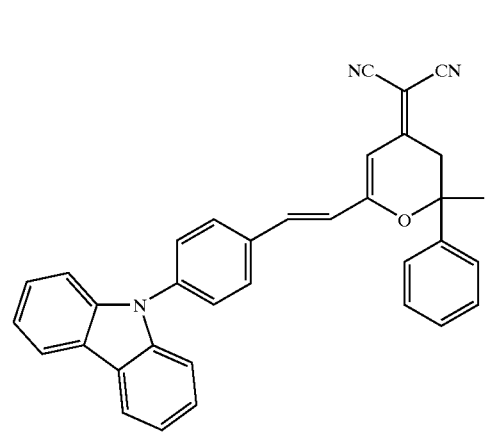
IV-35
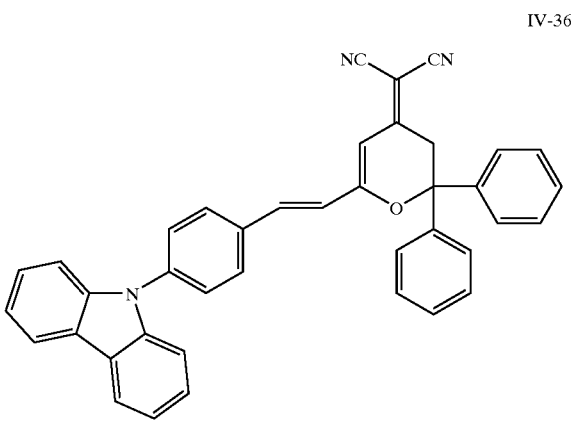
IV-36
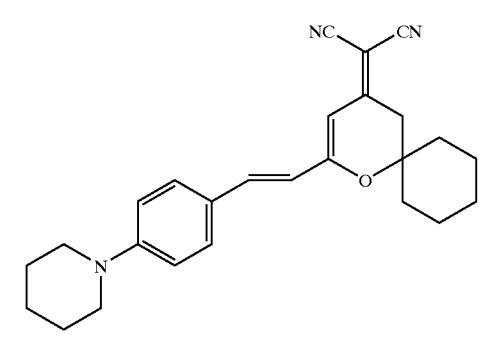
V-01

-continued
V-02
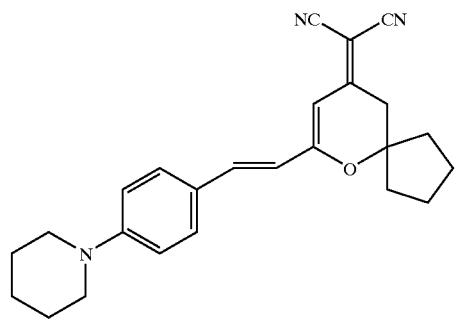
V-03
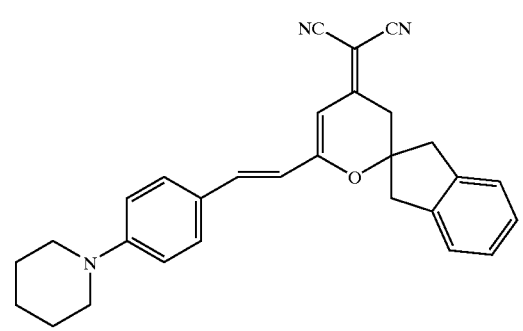
V-04
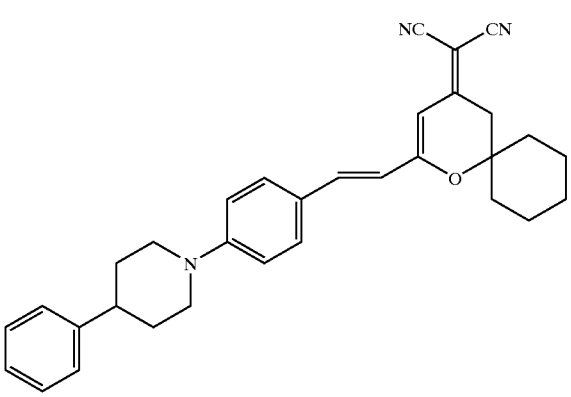
V-05
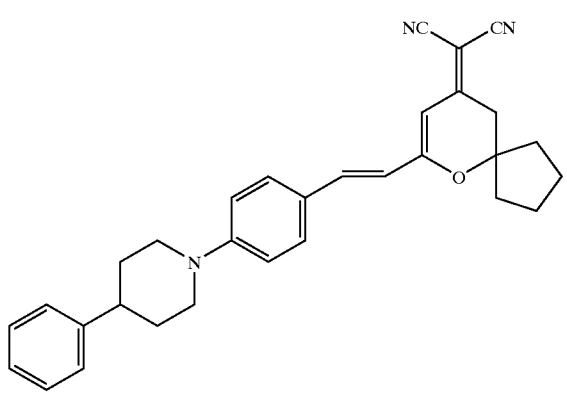
-continued
V-06
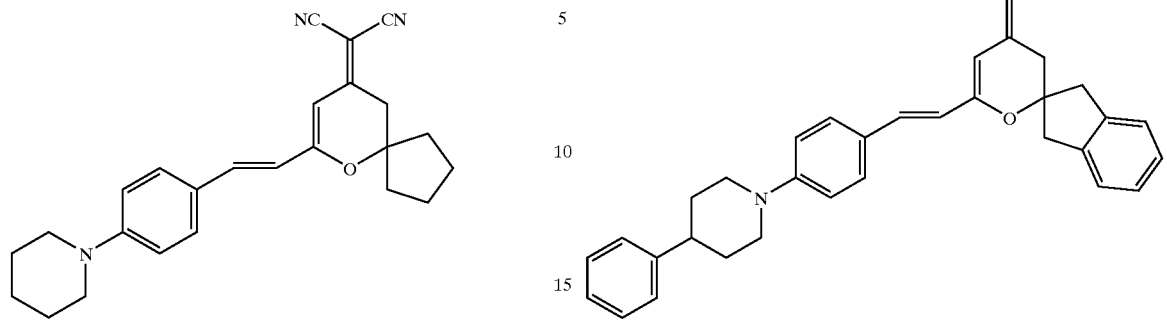
V-07
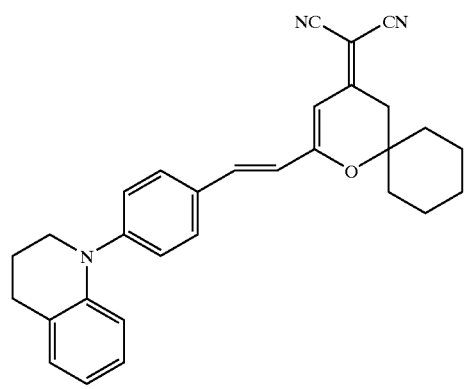
V-08
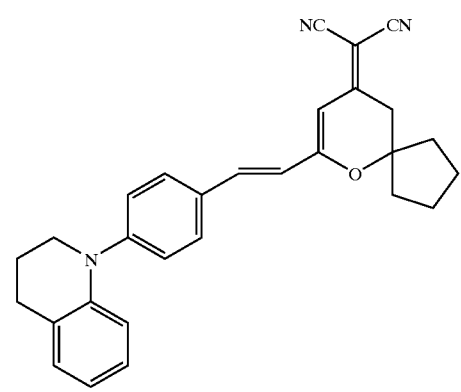
V-09
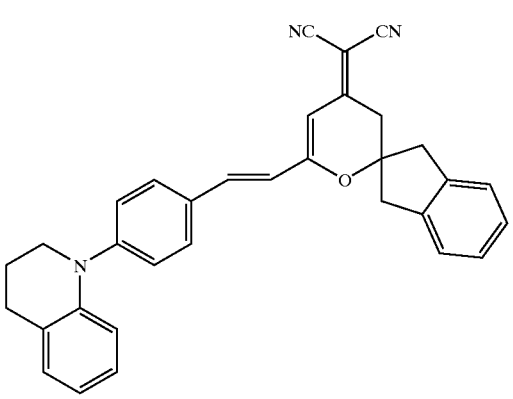

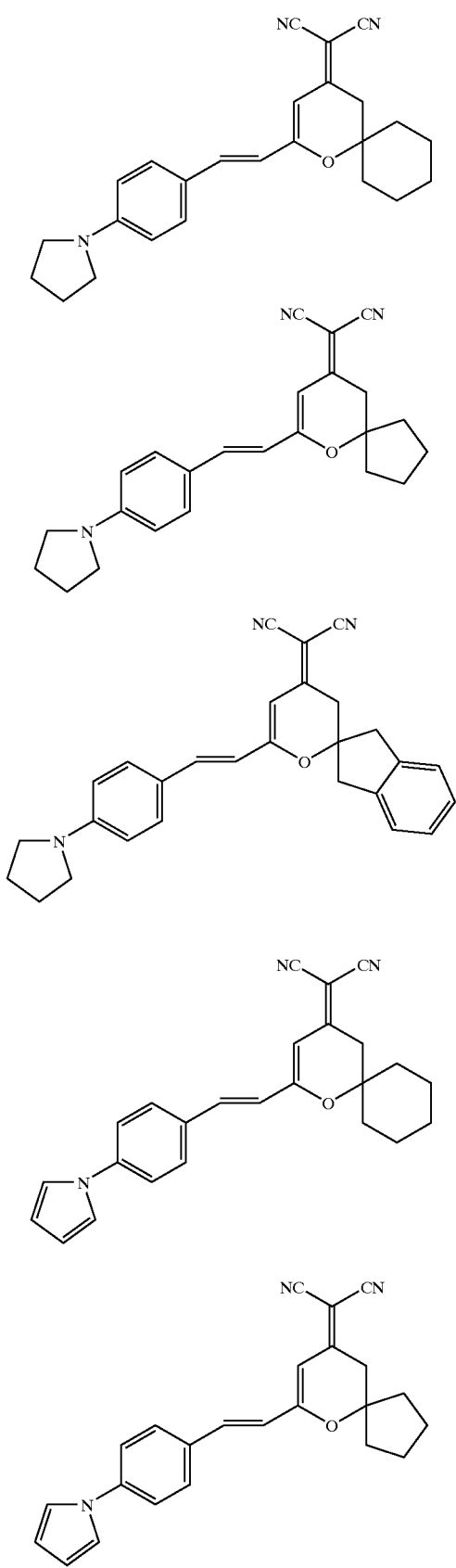
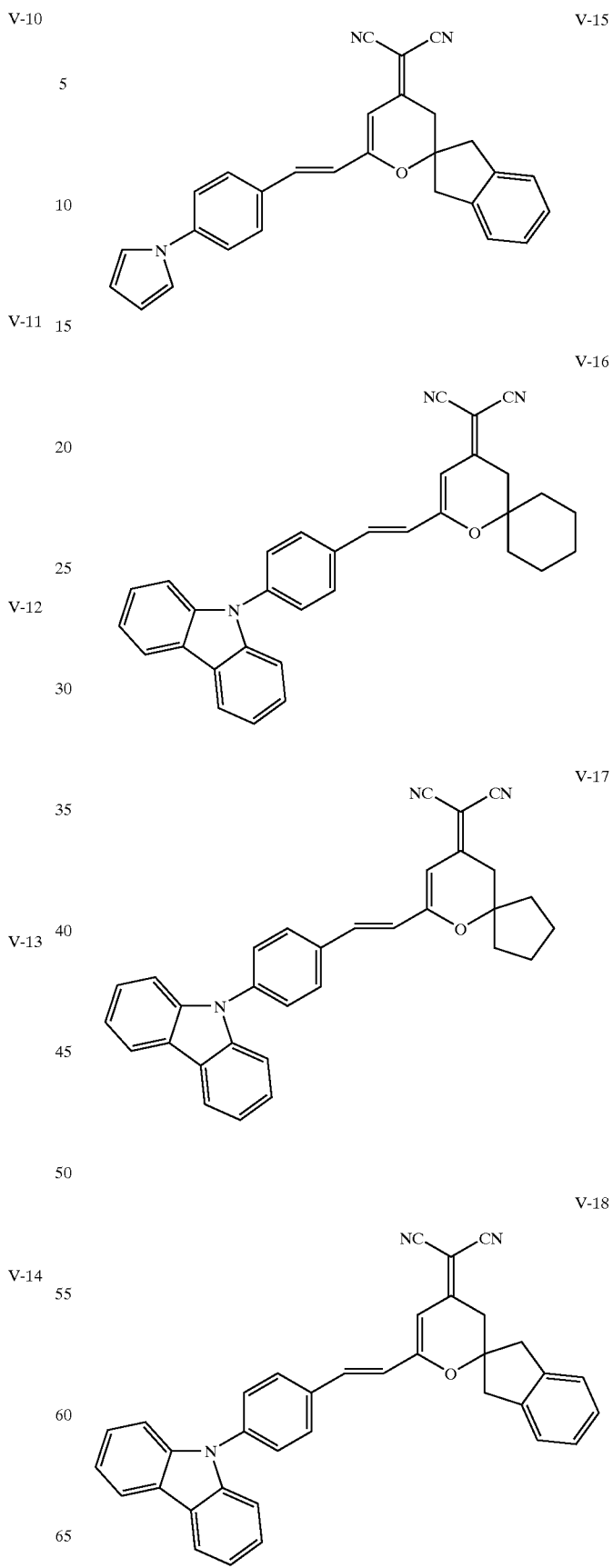

-continued
V-19
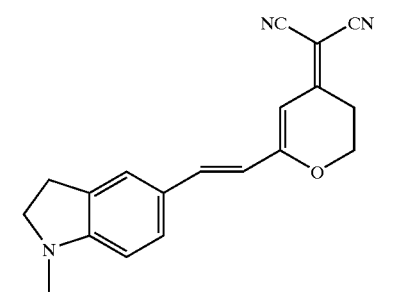
V-20
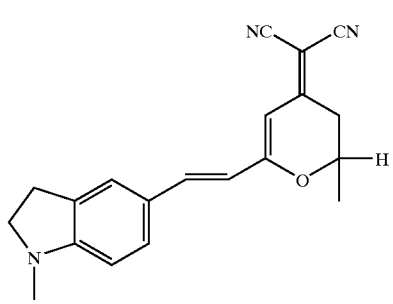
V-21
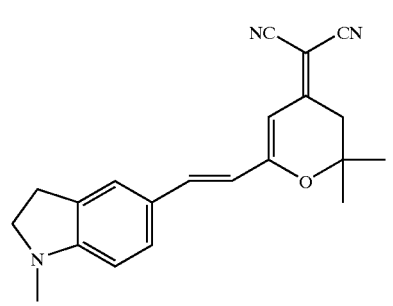
V-22
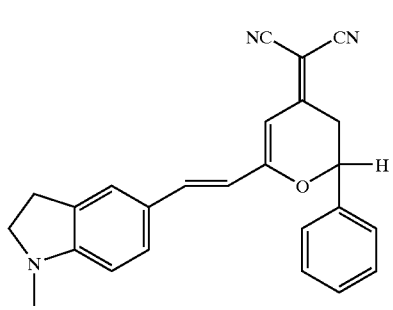
V-23
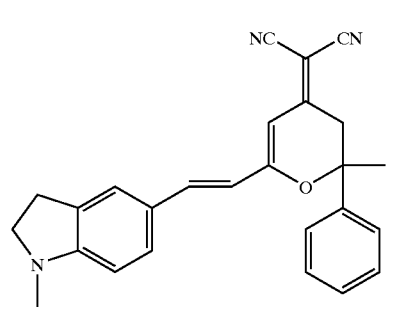
-continued
V-24
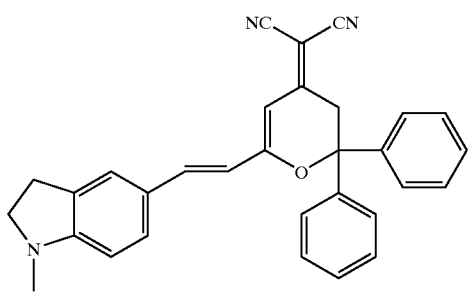
V-25
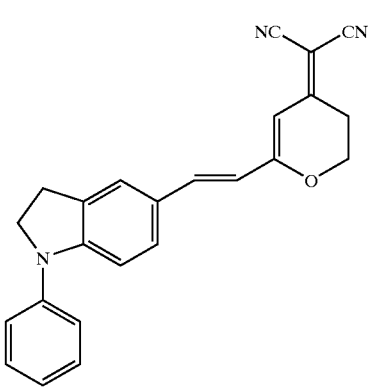
V-26
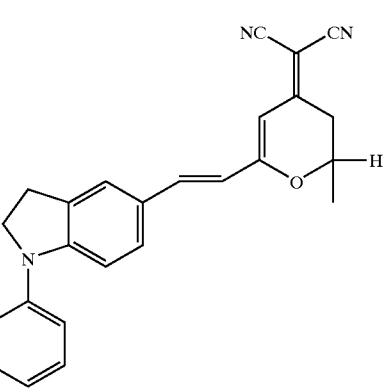
V-27
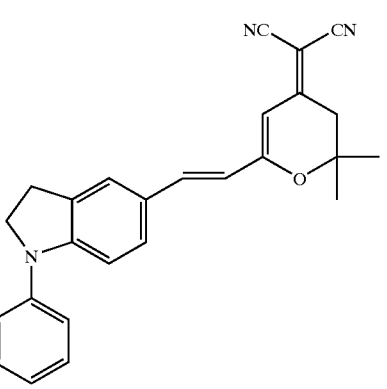

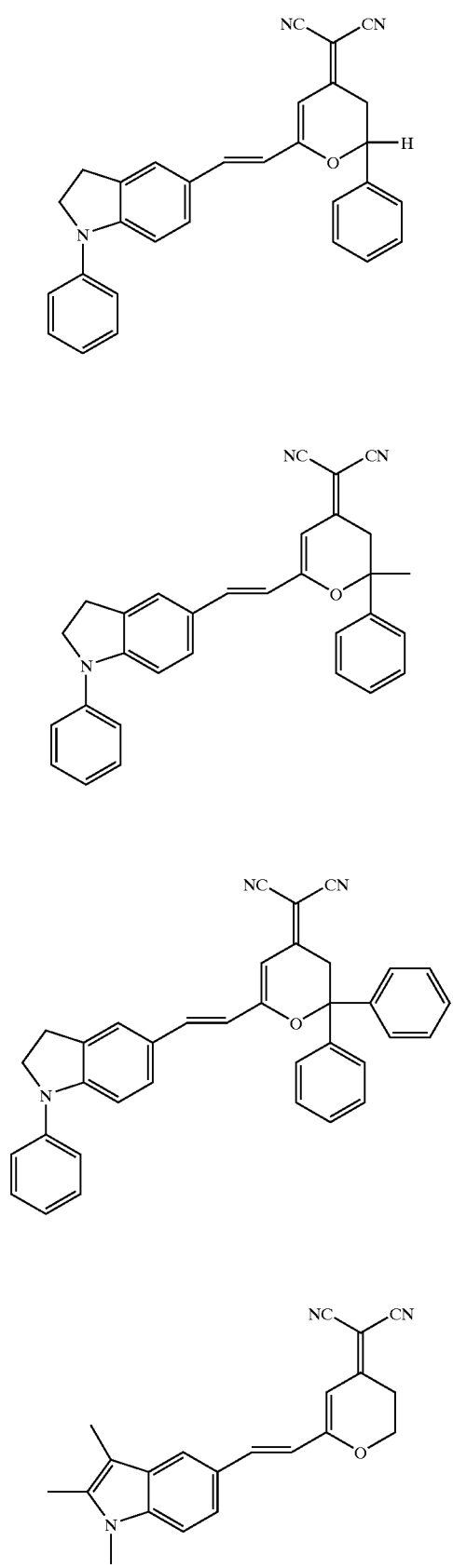

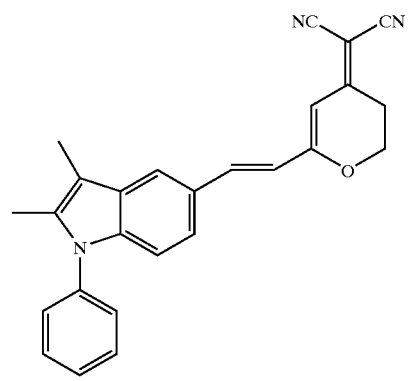 V-37
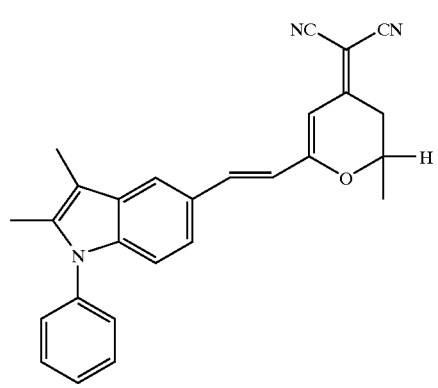 V-38
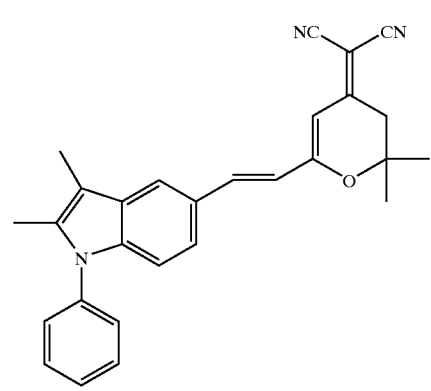 V-39
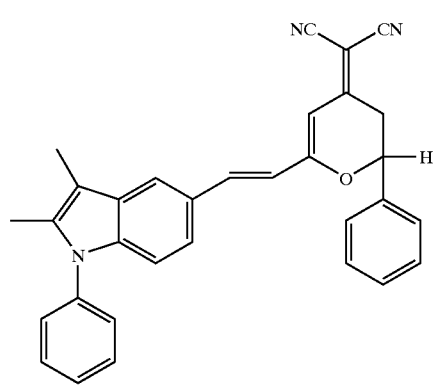 V-40
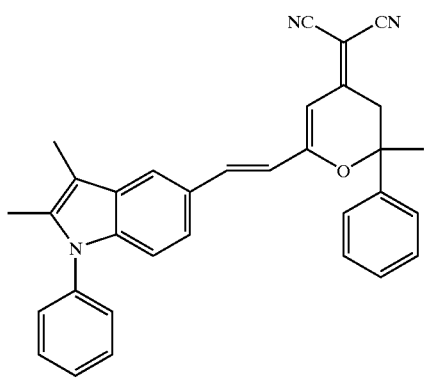 V-41
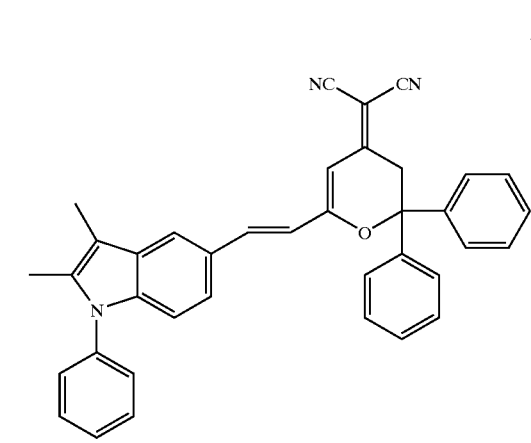 V-42
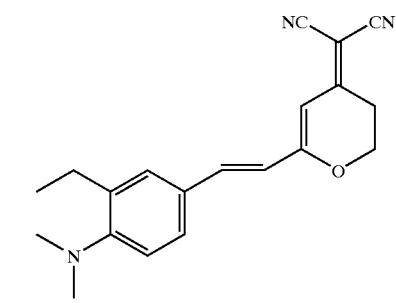 V-43
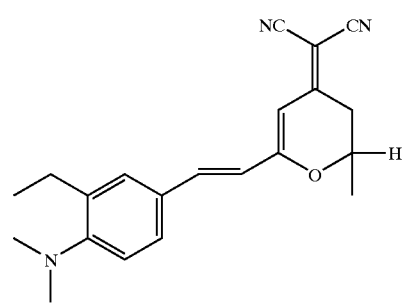 V-44

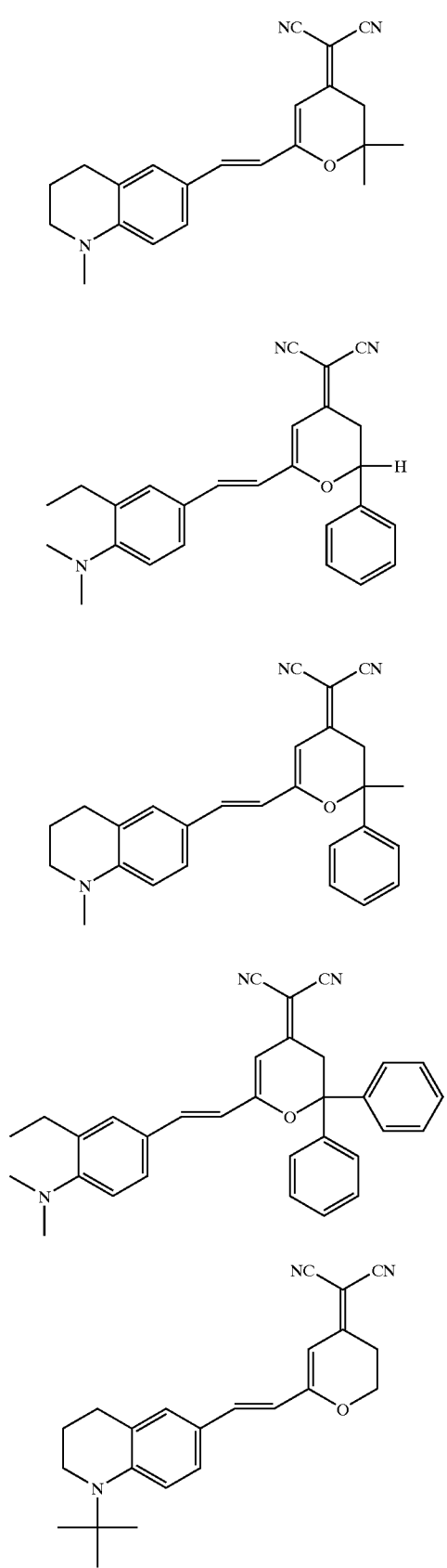
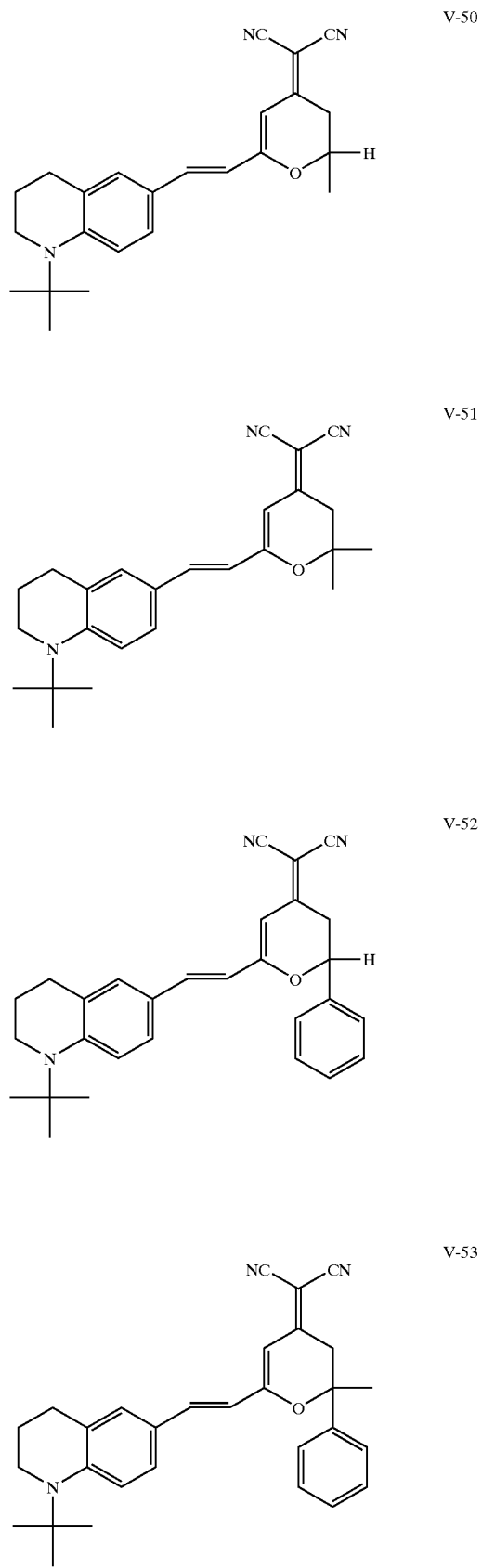

V-54 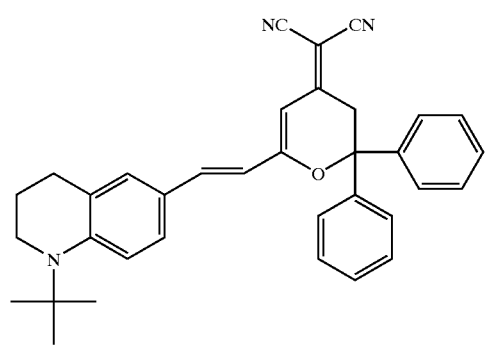
V-55 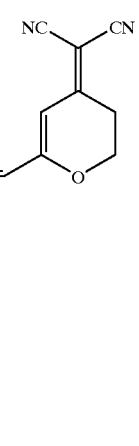
V-56 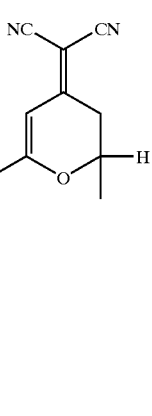
V-57 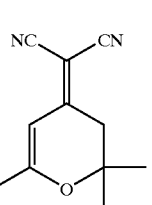
V-58 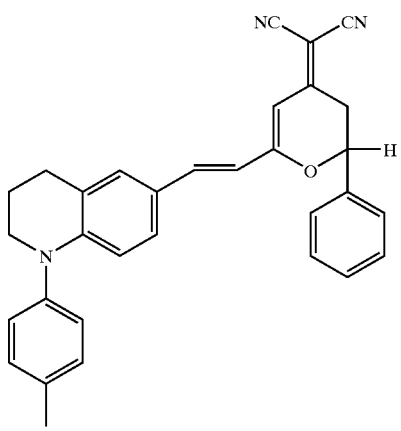
V-59 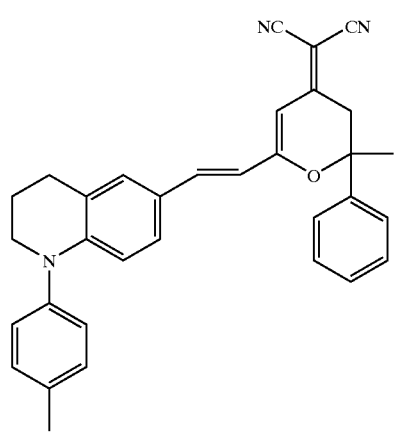
V-60 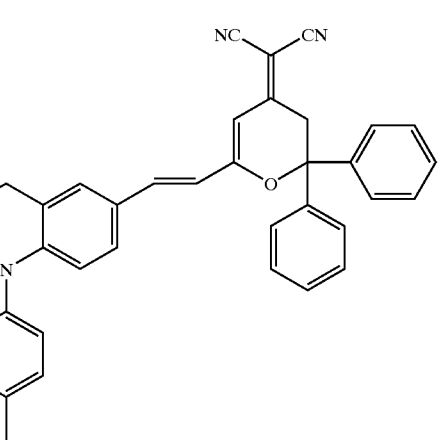
V-61 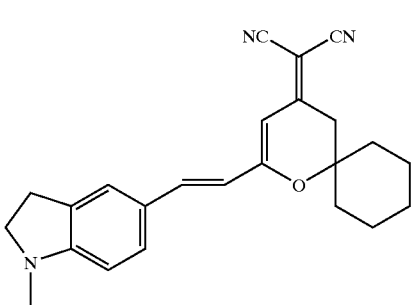

V-62 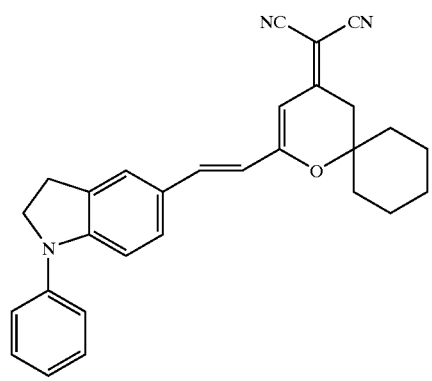
V-63 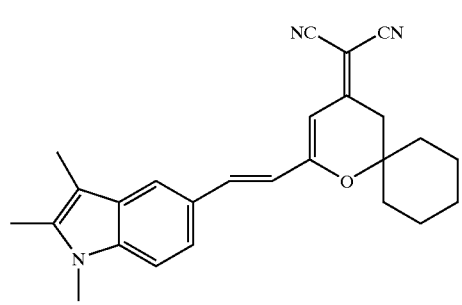
V-64 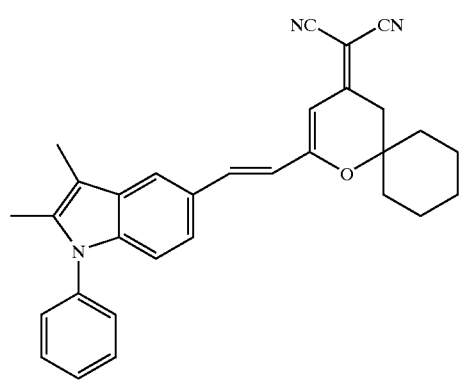
V-65 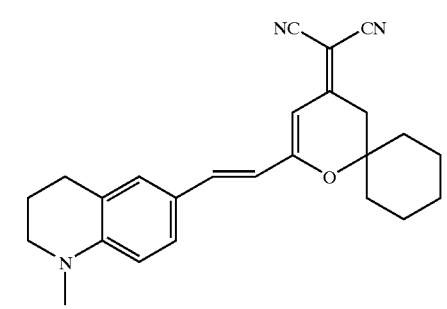
V-66 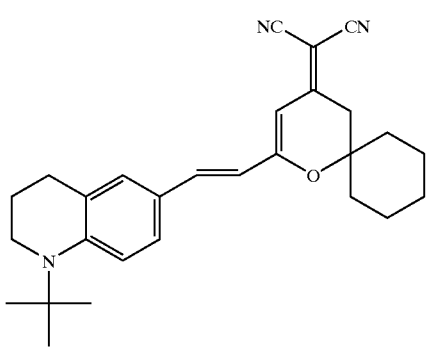
V-67 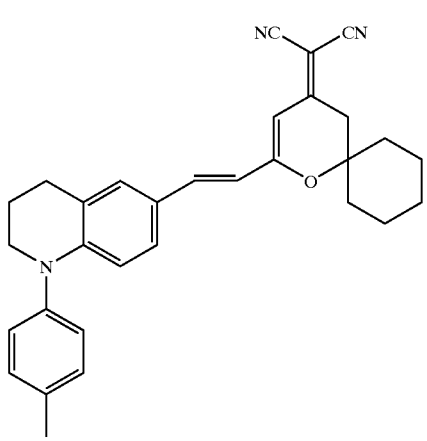
V-68 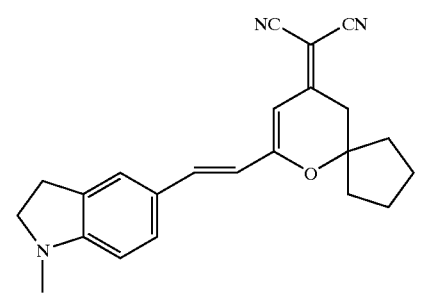
V-69 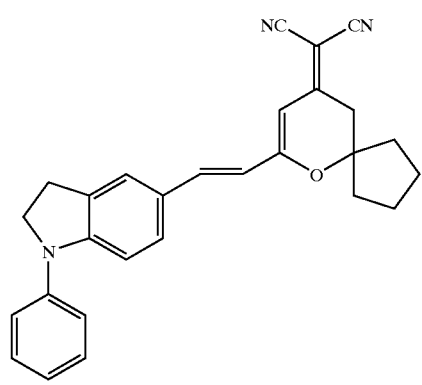

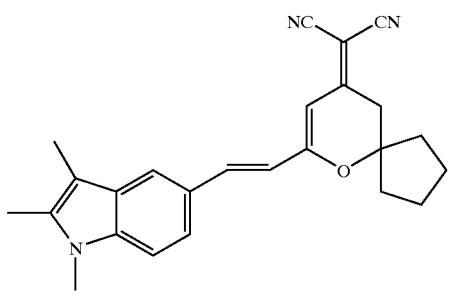
V-70
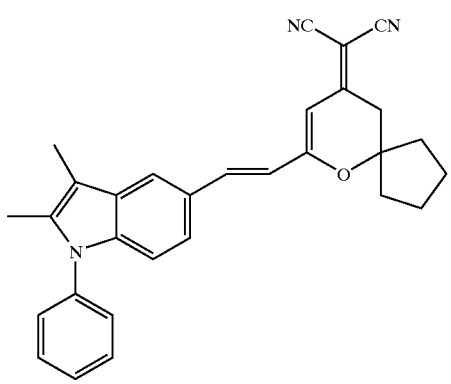
V-71
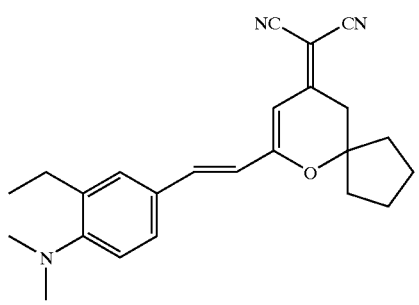
V-72
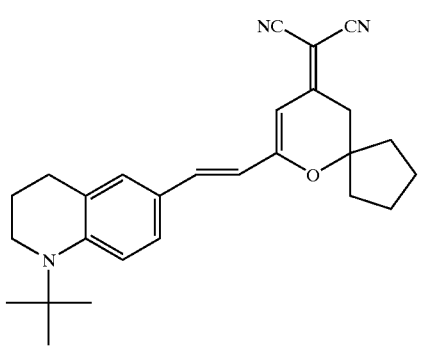
V-73
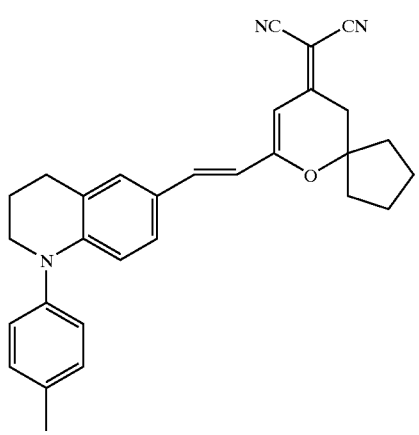
V-74
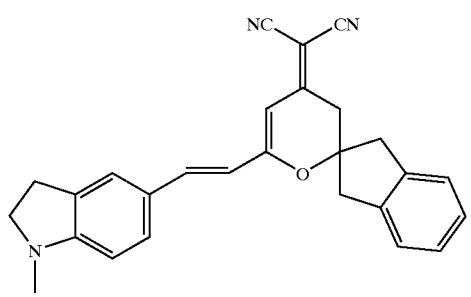
V-75
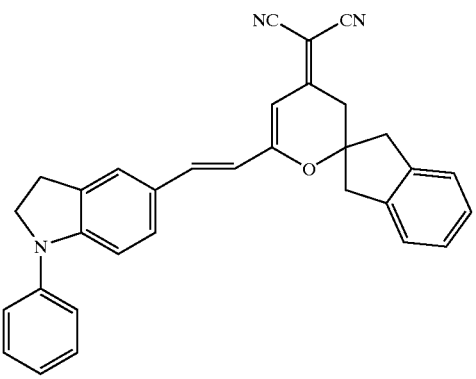
V-76
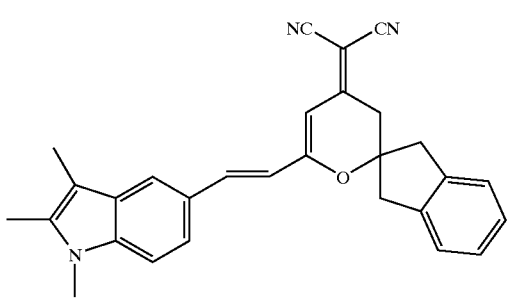
V-77

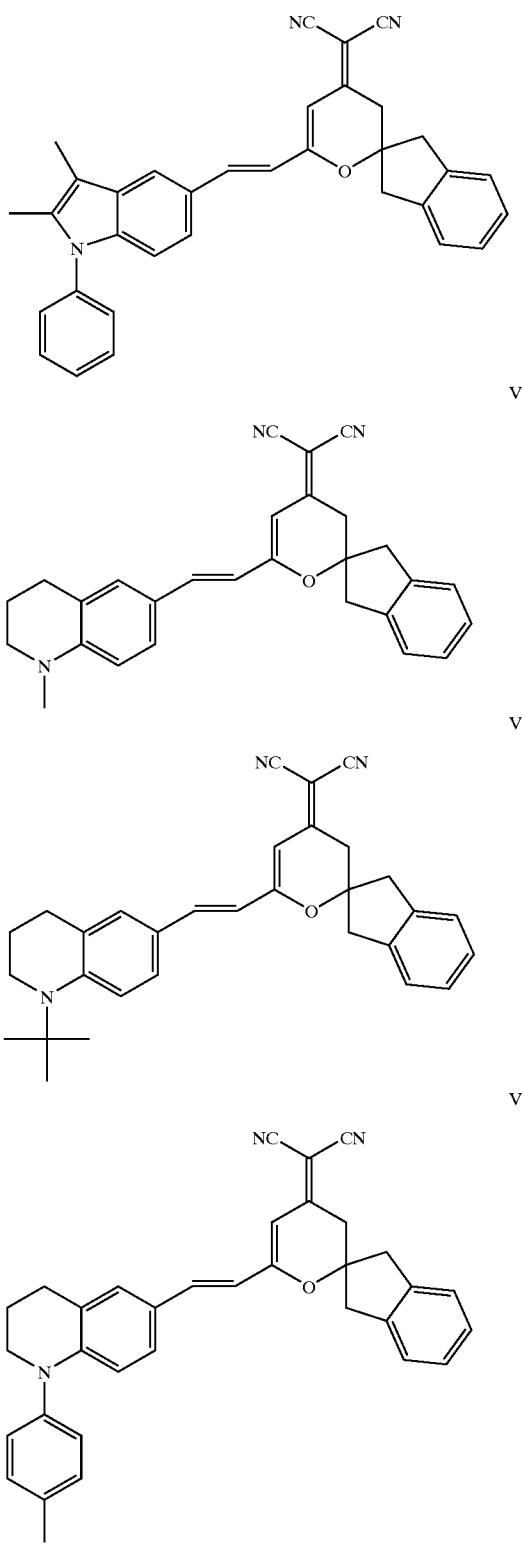

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described.

Other electron-transporting materials include various butadiene derivatives as disclosed in commonly-assigned U.S. Pat. No. 4,356,429 and various heterocyclic optical brighteners as described in commonly-assigned U.S. Patent No. 4,539,507. Benzazoles satisfying structural formula (G) are also useful electron transporting materials.

In some instances, light emitting layer 109 and electron transport layer 111 can optionally be collapsed into a single layer that serves the function of supporting both light emission and electron transportation.

Cathode

When light emission is through the anode, the cathode layer 113 used in this invention can include nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One preferred cathode material is comprised of a Mg:Ag alloy wherein the percentage of silver is in the range of 1 to 20%, as described in U.S. Pat. No. 4,885,221. Another suitable class of cathode materials includes bilayers comprised of a thin layer of a low work function metal or metal salt capped with a thicker layer of conductive metal. One such cathode is comprised of a thin layer of LiF followed by a thicker layer of Al as described in commonly-assigned U.S. Pat. No. 5,677,572. Other useful cathode materials include, but are not limited to, those disclosed in commonly-assigned U.S. Pat. Nos. 5,059,861; 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in commonly-assigned U.S. Pat. No. 5,776,623. Cathode materials can be deposited by evaporation, sputtering, or chemical vapor deposition. When needed, patterning can be achieved through many well known methods including, but not limited to, through-mask deposition, integral shadow masking as described in commonly-assigned U.S. Pat. No. 5,276,380 and EP 0 732 868, laser ablation, and selective chemical vapor deposition.

Deposition of Organic Layers

The organic materials mentioned above are suitably deposited through sublimation, but can be deposited from a solvent with an optional binder to improve film formation. If the material is a polymer, solvent deposition is usually preferred. The material to be deposited by sublimation can be vaporized from a sublimator "boat" often comprised of a tantalum material, e.g., as described in commonly-assigned U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (commonly-assigned U.S. Pat. No. 5,294,870), spatially-defined thermal dye transfer from a donor sheet (commonly-assigned U.S. Pat. Nos. 5,851,709 and 6,066,357) and inkjet method (commonly-assigned U.S. Pat. No. 6,066,357).

Encapsulation

Most OLED devices are sensitive to moisture and/or oxygen so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in commonly-assigned U.S. Pat. No. 6,226,890.

The entire contents of the patents and other publications referred to in this specification are incorporated herein by reference.

EXAMPLES

The invention has been described in detail with particular reference to certain preferred embodiments thereof, but it will be understood that variations and modifications can be effected within the spirit and scope of the invention.

Synthetic Scheme of 2,3-Dihydro-2,2,6-trimethyl-4H-pyran-4-one

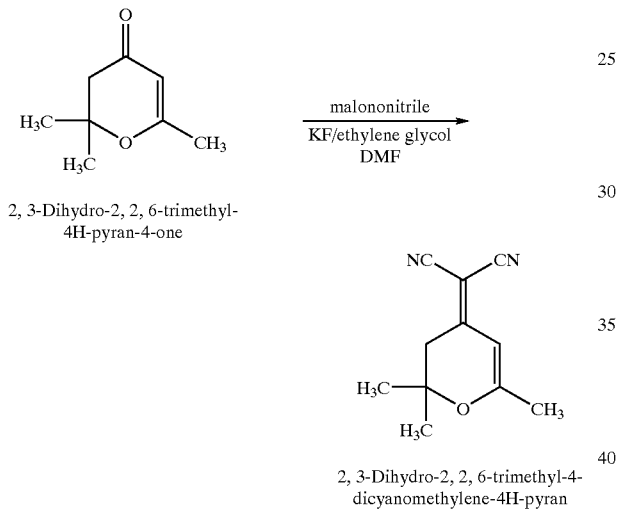

2, 3-Dihydro-2, 2, 6-trimethyl-4H-pyran-4-one 2, 3-Dihydro-2, 2, 6-trimethyl-4-dicyanomethylene-4H-pyran Ref.: Synthesis of 2,3-Dihydro-2,2,6-trimethyl-4H-pyran-4-one (synthesized according to: Peterson, John R.; Winter, Tamara J.; Miller Chris P, *Synthetic Communications*, 1988, 18(9), 949–963).

Example 1

Synthesis of 2,3-Dihydro-2,2,6-trimethyl-4-dicyanomethylene-4H-pyran

Potassium fluoride (13.6 g, 0.234 mol) dissolved in 65 ml ethylene glycol is added to a mixture of 2,3-diydro-2,2,6-trimethyl-4H-pyran-4-one (17.5 g, 0.125 mol) and malononitrile (47.3 g, 0.717 mol) in 65 ml DMF. The mixture is stirred overnight at room temperature during which time the mixture becomes dark red. After pouring to water, extracting with ether several times, drying over magnesium sulfate and concentration, the product is purified by column chromatography ($CH_2Cl_2$:Hexane/1:2) to afford 11.5 g (49% yield) of orange solid.

NMR: $^1$H-NMR ($CDCl_3$/TMS): δ 1.41 (s, 6H), 2.06 (s, 3H), 2.74 (s, 2H), 5.96 (s, 1H);

$^{13}$C-NMR ($CDCl_3$/TMS): δ=21.7, 25.4, 38.1, 70.6, 78.7, 98.8, 112.67, 113.4, 163.8, 169.6.

Synthetic Scheme of Examples 2–5

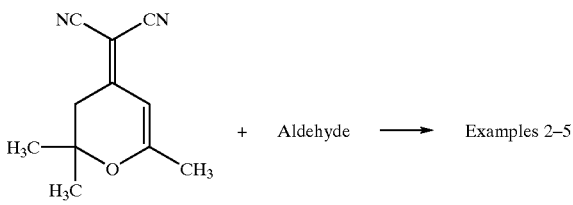

General Synthesis of Invented Red Luminescent Materials 4-dicyanomethylene-4H-pyran derivative (2.66 mmol), aldehyde (2.66 mmol), 5 drops piperidine in 12 ml toluene is heated at 110° C. overnight. Monitor by TLC until all starting materials have reacted. Cool to room temperature and remove toluene by rotary evaporation. Acetonitrile (30 ml) is added and after heating at 60° C. for 10 minutes, the mixture is cooled to 0° C. The solid is collected by vacuum filtration, washed with a minimum of ice cold acetonitrile and then washed with hexanes. The product is then dried to give pure red dopant. The red dopants were then identified using $^1$H-NMR and EI mass spectrometry.

The general synthesis procedure was used to synthesize examples 2–5. For examples 2–5, the pyran derivative used was 2,3-dihydro-2,2,6-trimethyl-4-dicyanomethylene-4H-pyran.

Example 2

Synthesis of 4-(Dicyanomethylene)-2,3-dihydro-2,2-dimethyl-6-(1,1,7,7-tetramethyljulolidyl-9-enyl)-4H-pyran Compound III-08 (TJDCP)

The aldehyde used in example 2 is:

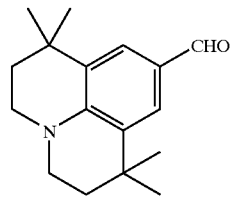

1, 1, 7, 7-tetramethyl-9-formyljulolidine

Example 3

Synthesis of 4-(Dicyanomethylene)-2,3-dihydro-2,2-dimethyl-6-julolidyl-9-enyl)-4H-pyran Compound III-07 (JDCP)

The aldehyde used in example 3 is:

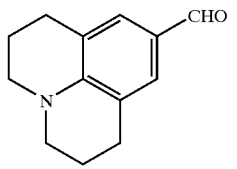

9-formyljulolidine

Example 4

Synthesis of 4-(Dicyanomethylene)-2,3-dihydro-2,2-dimethyl-6-(N,N-diethylbenzenamine-4-enyl)-4H-pyran Compound I-28 (DEDCP)

The aldehyde used in example 4 is:

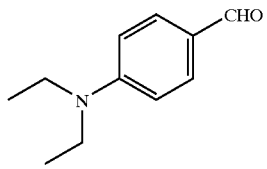

4-(diethylamino)benzaldehyde

Example 5

Synthesis of 4-(Dicyanomethylene)-2,3-dihydro-2,2-dimethyl-6-(N,N-diphenylbenzenamine-4-enyl)-4H-pyran Compound I-29 (DPDCP)

The aldehyde used in example 5 is:

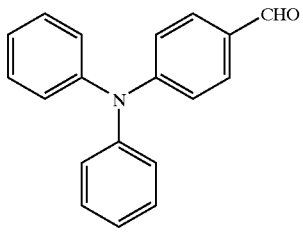

4-(diphenylamino)benzaldehyde

Table 1 lists some physical properties of a few examples of the new luminescent compounds.

TABLE 1

Physical Properties of Examples 2–6

| Red Dopants | $\lambda_{max.}$ abs.[b] | $\lambda_{max.}$ emis.[a, b] | $\Phi$[a, b, c] | H1 NMR (ppm)[d] | MS (m/z) |
|---|---|---|---|---|---|
| Example 2 TJDCP (III-08) | 549 nm | 651 nm | 0.77 | δ 1.3(s, 12H), 1.46(s,6H), 1.73–1.77 (t, 4H, $J_1$ = 6.01 Hz, $J_2$ = 6.15 Hz), 2.77(s, 2H), 3.28–3.32 (t, 4H, $J_1$ = 6.3 Hz, $J_2$ = 6.0 Hz), 6.12(s, 1H), 6.3–6.35 (d, 1H, J = 15.53 Hz), 7.23(s, 2H), 7.33–7.38 (d, 1H, J = 15.38 Hz) | 428 (M[+] + 1) |
| Example 3 JDCP (III-07) | 546 nm | 648 nm | 0.69 | $^1$H-NMR (CDCl3/TMS): δ 1.44(s, 6H), 1.92–2.0(p, 4H, $J_1$ = 6.15 Hz, $J_2$ = 5.57 Hz, $J_3$ = 6.15 Hz, $J_4$ = 6.29 Hz), 2.71–2.75(m, 6H), 3.24–3.28(t, 4H, $J_1$ = 5.86 Hz, $J_2$ = 5.56 Hz), 6.07(s, 1H), 6.27–6.32(d, 1H, J = 15.37 Hz), 6.99(s, 2H), 7.27–7.32 (d, 1H, J = 15.52 Hz) | 372 (M[+] + 1) |
| Example 4 DEDCP (I-28) | 514 nm | 613 nm | 0.38 | $^1$H-NMR (CDCl3/TMS): δ 1.18–1.23 (t, 6H, $J_1$ = 7.17 Hz, $J_2$ = 7.03 Hz), 1.46(s, 6H), 2.78 (s, 2H), 3.38–3.45(q, 4H, $J_1$ = 7.18 Hz, $J_2$ = 7.03 Hz, $J_3$ = 7.17 Hz), 6.11(s, 1H), 6.31–6.37(d, 1H, J = 15.52 Hz), 6.63–6.66(d, 2H, J = 9.08 Hz), 7.34–7.39 (d, 1H, J = 15.23 Hz), 7.38–7.41 (d, 2H, J = 8.93 Hz) | 348 (M[+] + 1) |
| Example 5 DPDCP (I-29) | 498 nm | 643 nm | 0.55 | $^1$H-NMR (CDCl3/TMS): δ 1.47(s, 6H), 2.8(s, 2H), 6.14(s, 1H), 6.41–6.46 (d, 1H, J = 15.82 Hz), 6.98–7.01(d, 2H, J = 8.64 Hz), 7.09–7.15(m, 5H), 7.26–7.37(m, 8H) | 444 (M[+] + 1) |

[a] $\lambda_{exc.}$ 520 nn
[b] Solvent: $CH_2Cl_2$
[c] relative to DCJTB
[d] solvent: $CDCl_3$/TMS General Procedures for Prepare EL Devices:

These examples illustrates the advantage of fabricating an organic EL device where the EL medium contains the red fluorescent TJDCP (compound III-08) doped luminescent layer. The organic EL medium has four organic layers, namely, a hole injection layer, a hole transport layer, a doped luminescent layer, and an electron transport layer.

a) An indium tin oxide (ITO) coated glass substrate was sequentially ultrasonicated in a commercial detergent, rinsed in deionized water, degreased in toluene vapor and exposed to ultraviolet light and ozone for a few minutes. Then followed a treatment by polymeric fluoro substituted chemicals.

b) Onto the above treated ITO glass substrate was deposited a hole transport layer of N,N'bis(1-naphthyl)N,N'diphenylbenzidine (750 Å), also by evaporation from a tantalum boat.

c) A layer of doped Alq (375 Å) was then deposited onto the hole transport layer. The doped layer contains the red fluorescent material which was codeposited with Alq to form a uniform doped luminescent layer.

c) An electron transport layer of Alq (350 Å) was then deposited onto the luminescent layer.

d) On top of the Alq layer was deposited a cathode layer (2200 Å) formed of a 10:1 atomic ratio of Mg and Ag.

The above sequence completed the deposition of the EL device. The device was then hermetically packaged in a dry glove box for protection against ambient environment.

Table 2 lists EL device performance prepared by above procedures.

TABLE 2

EL Device Performance
ITO/NPB 750 Å /LEL 375 Å /ETL 375 Å /Mg:Ag 2000 Å

| EL | LEL | CIE X | CIE Y | cd/m$^2$ |
|---|---|---|---|---|
| Example 6[a] | Alq + 2% TJDCP (III-08) | 0.63 | 0.35 | 37 |
| Example 7[b] | Alq + 1% TJDCP (III-08) | 0.65 | 0.34 | 69 |
| Example 8[b] | Alq + 2% TJDCP (III-08) | 0.68 | 0.31 | 29 |
| Example 9[a] | Alq + 5% Rubrene + 0.5% TJDCP (III-08) | 0.66 | 0.33 | 140 |
| Example 10[a] | Alq + 5% Rubrene + 1% TJDCP (III-08) | 0.67 | 0.32 | 72 |
| Example 11[a] | Alq + 5% Rubrene + 2% TJDCP (III-08) | 0.66 | 0.32 | 42 |
| Example 12[a] | Alq + 5% Rubrene + 3% TJDCP (III-08) | 0.67 | 0.32 | 31 |

All cells run at 20 mA/cm$^2$
[a]ETL = Alq
[b]ETL = TPBI

The light output from these EL devices ranged from 30 cd/m$^2$ to 140 cd/m$^2$ when it was driven by a current source of 20 mA/cm$^2$ and a bias voltage of about 7 volts. The EL color is red with 1931 CIE color and the EL spectrum indicates that emission originates from the red fluorescent dye doped Alq layer and is predominantly characteristic of the red dopant. The red color of electroluminescence of these devices are more saturated than that of DCJT and DCJTB doped devices driven under similar conditions described in the previous example.

The invention has been described in detail with particular reference to certain preferred embodiments thereof, but it will be understood that variations and modifications can be effected within the spirit and scope of the invention.

PARTS LIST

100 EL Device
101 Substrate
103 Conductive Anode layer
105 Hole-Injecting layer (HIL)
107 Hole-Transporting layer (HTL)
109 Light-Emitting layer (LEL)
111 Electron-Transporting layer (ETL)
113 Cathode

What is claimed is:

1. An organic EL device, comprising an anode and a cathode, and at least one organic luminescent medium including a compound of the formula:

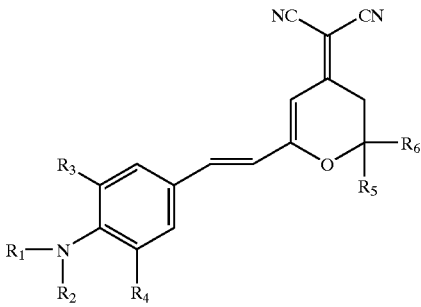

wherein:

R1 and R2 are individually alkyl of from 1 to 20 carbon atoms, aryl, substituted aryl, carbocyclic, heterocyclic, or substituted heterocyclic or R1 and R2 can be connected to form 5 or 6 membered rings which may be substituted or unsubstituted, and R3 and R4 are individually hydrogen, alkyl of from 1 to 10 carbon atoms, or a branched or unbranched 5 or 6 membered substituent ring connecting with R1, R2 respectively; and R5 and R6 are individually hydrogen, alkyl of from 1 to 20 carbon atoms; aryl or heteroaryl of from 5 to 24 carbon atoms, or R6 can be connected with R5 to form a branched or unbranched 5 or 6 membered carbocyclic ring.

2. The organic EL device of claim 1 wherein the compound has the formula:

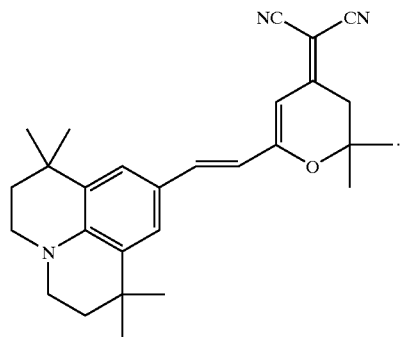

3. The organic EL device of claim 1 wherein the compound has the formula:

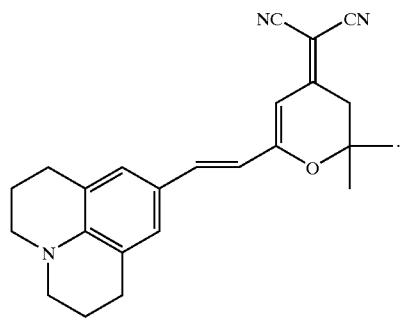

4. The organic EL device of claim 1 wherein the compound has the formula:

5. The organic EL device of claim 1 wherein the compound has the formula:
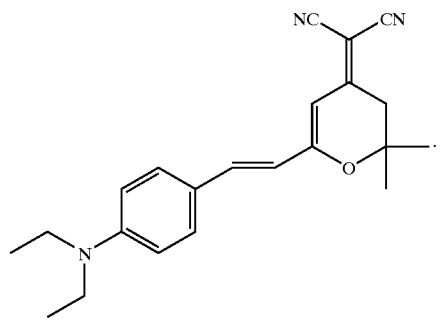
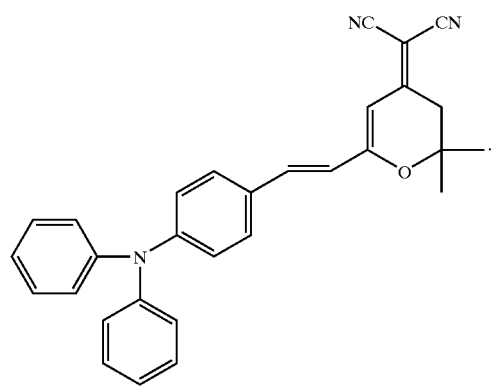
* * * * *